(12) United States Patent
Romfh et al.

(10) Patent No.: US 12,716,847 B2
(45) Date of Patent: Aug. 25, 2026

(54) DONOR ORGAN VIABILITY MONITORING USING RAMAN SPECTROSCOPY

(71) Applicant: Pendar Technologies, Inc., Cambridge, MA (US)

(72) Inventors: John P. Romfh, Palo Alto, CA (US); Daryoosh Vakhshoori, Cambridge, MA (US); Peili Chen, Andover, MA (US); Shannon Tessier, Ashland, MA (US); Reinier De Vries, Utrecht (NL); Stephanie Cronin, Boston, MA (US)

(73) Assignees: Pendar Technologies, Inc., Cambridge, MA (US); The General Hospital Corporation, Boston, MA (US)

( * ) Notice: Subject to any disclaimer, the term of this patent is extended or adjusted under 35 U.S.C. 154(b) by 390 days.

(21) Appl. No.: 18/063,901

(22) Filed: Dec. 9, 2022

(65) Prior Publication Data

US 2023/0109459 A1 Apr. 6, 2023

Related U.S. Application Data

(63) Continuation of application No. PCT/US2021/036932, filed on Jun. 11, 2021.

(Continued)

(51) Int. Cl.
*G01N 21/65* (2006.01)
*A61B 5/00* (2006.01)

(52) U.S. Cl.
CPC .......... *G01N 21/658* (2013.01); *A61B 5/0075* (2013.01); *G01N 2201/06113* (2013.01)

(58) Field of Classification Search
CPC ........ G01N 21/658; G01N 2201/06113; A61B 5/007
See application file for complete search history.

(56) References Cited

U.S. PATENT DOCUMENTS 6,961,599 B2 11/2005 Lambert et al.
8,253,936 B2 8/2012 Cohen et al.

(Continued)

FOREIGN PATENT DOCUMENTS

WO 1999047922 A2 9/1999
WO 2008150587 A2 12/2008
WO WO-2019060427 A1 * 3/2019 ............ G16H 50/30

OTHER PUBLICATIONS

Zu, T.N., Athamneh, A.I., Collakova, E., Robertson, J., Hawken, T., Aardema, C. and Senger, R.S., 2015. Assessment of ex vivo perfused liver health by Raman spectroscopy. Journal of Raman Spectroscopy, 46(6), pp. 551-558. (Year: 2015).*

(Continued)

*Primary Examiner* — Michelle M Iacoletti
*Assistant Examiner* — Mohamed Doumbia
(74) *Attorney, Agent, or Firm* — Smith Baluch LLP

(57) ABSTRACT

The present technology includes a system and method for monitoring a donor organ tissue using Raman spectroscopy. The technology enables real-time quantification of the mitochondrial redox state in the tissue sample taken from an organ intended for transplant using a compact device. The system is based on resonance Raman spectroscopy which can quantify a mitochondrial redox state in tissues using a Resonance Raman Reduced Mitochondrial Ratio. The mitochondrial redox state of the tissue sample acts as a marker of tissue function and may distinguish healthy versus damaged tissue. Moreover, these measures may correlate with transplantation outcomes.

17 Claims, 19 Drawing Sheets

Related U.S. Application Data

(60) Provisional application No. 63/038,232, filed on Jun. 12, 2020.

(56) References Cited

U.S. PATENT DOCUMENTS

| | | | | |
|---|---|---|---|---|
| 8,304,181 | B2 | 11/2012 | Hassanein et al. | |
| 8,553,732 | B2 | 10/2013 | Maier et al. | |
| 8,765,364 | B2 | 7/2014 | Curtis et al. | |
| 9,055,740 | B2 | 6/2015 | Hassanein et al. | |
| 10,575,515 | B2 * | 3/2020 | Yarmush | A01N 1/0226 |
| 10,697,894 | B2 | 6/2020 | Schütze et al. | |
| 2008/0286747 | A1 * | 11/2008 | Curtis | G01N 33/5088 705/2 |
| 2010/0034743 | A1 | 2/2010 | Cohen et al. | |
| 2014/0340675 | A1 | 11/2014 | Takamatsu et al. | |
| 2015/0079580 | A1 | 3/2015 | Hassanein et al. | |
| 2017/0202462 | A1 | 7/2017 | Motz et al. | |
| 2018/0073984 | A1 | 3/2018 | Schütze et al. | |
| 2020/0015724 | A1 * | 1/2020 | Matsui | A61B 5/6803 |
| 2020/0375178 | A1 | 12/2020 | Becker et al. | |

OTHER PUBLICATIONS

Brazhe (2013. In situ Raman study of redox state changes of mitochondrial cytochromes in a perfused rat heart. PLoS One, 8(8), p. e70488) (Year: 2013).*

Zu (Zu, 2015. Assessment of ex vivo perfused liver health by Raman spectroscopy. Journal of Raman Spectroscopy, 46(6), pp. 551-558.) (Year: 2015).*

Bar-Or et al. "Raman spectral signatures of human liver perfusates correlate with oxidation reduction potential." Molecular medicine reports 2.2 (2009): 175-180.

Brazhe et al., "In situ Raman study of redox state changes of mitochondrial cytochromes in a perfused rat heart." PLoS One 8.8 (2013): e70488. 9 pages.

Bruinsma et al., "Peritransplant energy changes and their correlation to outcome after human liver transplantation." Transplantation 101.7 (2017): 1637, 8 pages.

Cypel et al., "Normothermic ex vivo perfusion prevents lung injury compared to extended cold preservation for transplantation." American Journal of Transplantation 9.10 (2009): 2262-2269.

De Vries et al., "Real-Time Viability Assessment During Normothermic Machine Perfusion With Raman Spectroscopy." American Transplant Congress Meeting Abstract May 30, 2020. 4 pages.

Ember et al. "Raman spectroscopy and regenerative medicine: a review." NPJ Regenerative medicine 2.1 (2017): 12, 10 pages.

Feng et al., "Characteristics associated with liver graft failure: the concept of a donor risk index." American Journal of Transplantation 6.4 (2006): 783-790.

Flores et al., "The donor risk index: A decade of experience." Liver Transplantation 23.9 (2017): 1216-1225.

Higashi et al., "Restoration of ATP contents in the transplanted liver closely relates to graft viability in dogs." European surgical research 21.2 (1989): 76-82.

International Search Report and Written Opinion in International Patent Application No. PCT/US2021/036932 mailed Oct. 4, 2021, 8 pages.

Perry et al., "Responsive monitoring of mitochondrial redox states in heart muscle predicts impending cardiac arrest." Science translational medicine 9.408 (2017). 12 pages.

Vuiblet et al. "Raman-based detection of hydroxyethyl starch in kidney allograft biopsies as a potential marker of allograft quality in kidney transplant recipients." Scientific Reports 6.1 (2016): 33045, 9 pages.

Zu et al. "Assessment of ex vivo perfused liver health by Raman spectroscopy." Journal of Raman Spectroscopy 46.6 (2015): 551-558.

* cited by examiner

DONOR ORGAN VIABILITY MONITORING USING RAMAN SPECTROSCOPY

CROSS-REFERENCE TO RELATED APPLICATION(S)

This application is a bypass continuation of PCT/US2021/036932, filed on Jun. 11, 2021, which claims the priority benefit, under 35 U.S.C. 119(e), of U.S. Application No. 63/038,232, filed Jun. 12, 2020. Each of these applications is incorporated herein by reference in its entirety for all purposes.

BACKGROUND

End-stage organ disease contributes to 730,000 deaths annually in the US alone and transplantation is often the only treatment option. Although a record-breaking number of 34,768 transplants were performed in the US in 2017, they are nowhere close to meeting demand, resulting in a severe donor organ shortage. For example, although liver failure is estimated to cause 60,000 deaths per year, merely 12,000 patients are listed on the liver transplant wait-list and of these, only 8,000 will receive a transplant each year in the US. These estimates of death attributable to an inadequate organ supply are conservative, as the true demand is significantly higher as many potential candidates never reach the waiting list and because indications for transplant would be greatly expanded with organ availability. Thus, improving access to this lifesaving treatment option has become an immediate necessity.

Paradoxically, the donor organ shortage is not caused solely by a limited availability of cadaveric organs-more than 25% of donor livers procured for transplantation are not ultimately transplanted. Also, it is estimated that there is an additional donor pool of 6,000 unprocured livers/year, of which many are only marginally damaged. However, because of their uncertain viability, none of these potential donor organs are used while transplantation of just a fraction of these organs would be enough to dramatically reduce the organ shortage.

To overcome the shortage, "extended criteria liver grafts," including grafts from older donors, steatotic grafts, donors after circulatory death (DCD), and grafts with prolonged cold storage are being more commonly transplanted. However, transplantation of these marginal grafts can have long-term consequences for the recipient—evidence suggests suboptimal marginal grafts are correlated with reduced patient and graft survival. Thus, a significant barrier in being able to safely and confidently utilize extended criteria organs to solve the organ shortage is defining the criteria that can be extended. This goal is significantly complicated by the high degree of donor-to-donor variability and the fact that compounding stressors are incurred on the organ throughout the handling process. Further, organ allocation is already severely restricted by time, therefore, these criteria need to be ascertained and defined for each organ rapidly and preferably in real-time. Taken together, a critical bottleneck to the safe utilization of marginal organs to solve the organ shortage is the identification of biomarkers for the assessment of organ fitness.

FIG. 1 shows a timeline for organ donation after circulatory death (top) and after brain death (bottom). The process of organ donation includes a warm ischemia time (WIT) in the donor, retrieval, preservation at low temperature (e.g., 4° C.), and WIT in the recipient. Optimal liver handling for transplantation is critical, beginning with retrieval from the donor, and continuing during storage and transport and finally reperfusion during transplant to the recipient. Each of these stages in organ handling has the potential to cause injury and these compounding injuries subsequently effect long-term graft survival. In general, retrieval of organs from donors after brain death (DBD) is preferable since organs remain perfused with oxygenated blood until the point of organ retrieval. These organs have a shorter WIT in the donor. In contrast, donors after circulatory death (DCD) are inevitably exposed to a greater duration of WIT since heart and blood perfusion stops. While approximately 8.9% of total transplants currently use organs from DCD (maximum warm ischemia time for a transplanted DCD liver is 30 min), it is estimated that every year ~6,000 livers fall into the category of "marginally injured" warm ischemic livers (between 30-60 min warm ischemia). However, without any means for rapid, real-time assessment of organ fitness, these organs cannot be safely utilized and are discarded. Inevitably, some of these life-saving organs are fit for transplant but instead are discarded unnecessarily.

The need for rapid assessment of organ fitness would also be beneficial in subsequent stages of organ handling. Current clinical standards for organ preservation and transport use static hypothermic storage at 4° C. (immersed in ice-cold University of Wisconsin (UW) solution); however, this method only moderately slows down tissue deterioration. The maximum allotted cold ischemia time is typically 12 hours based on current guidelines. Despite these time constraints and due to desperation to overcome the organ shortage, grafts with prolonged periods of cold storage are being more readily transplanted. However, these sub-optimal conditions may affect the quality of transplanted organs, with inferior patient outcomes for organs damaged by cold ischemia. Further, these marginal organs may have also suffered additional upstream injuries such as warm ischemia or other unfavorable donor characteristics which increase the risk to the recipient.

SUMMARY

Traditional factors used to determine a donor organ's viability for transplant include donor characteristics such as obesity, age, steatosis, high level of ALT (alanine aminotransferase) or AST (aspartate aminotransferase), etc., or others such as warm and cold ischemia time. An improved approach is to use a single quantitative parameter to assess a donor organ's viability in real-time. Resonance Raman spectroscopy can be used to quantify a mitochondrial redox state in a donor organ. The mitochondrial redox state can be used to distinguish healthy and damaged tissue in the donor organ, thereby determining the donor organ's viability.

Embodiments of the present technology include a method of monitoring a biological tissue. The method of monitoring a biological tissue includes warming a perfusate, perfusing the biological tissue with the perfusate, measuring a series of Raman spectra of the biological tissue, quantifying a series of reduced mitochondrial ratios from the series of Raman spectra, and determining a viability of the biological tissue based on the series of reduced mitochondrial ratios. The viability determination based on Raman spectra may be used instead of or in addition to the traditional factors used to determine a donor organ's viability for transplant.

Measuring a series of Raman spectra of the biological tissue may include measuring a Raman spectrum over 1 hour. The biological tissue may be a donor organ intended for transplant. The biological tissue may be from an organ biopsy. The organ biopsy may be of a donor organ intended for transplant. The donor organ may be a liver, heart, kidney, or lung.

Quantifying the series of reduced mitochondrial ratios may include analyzing the series of Raman spectra using a reference library. The method of monitoring a biological tissue may include predicting a probability of rejection of the organ by a patient based on the viability of the biological tissue. Warming the perfusate may include warming the perfusate to 37° C. Measuring the series of Raman spectra may include contacting the biological tissue with a probe. Measuring the series of Raman spectra may include making stand-off Raman spectra measurements. The perfusate may include at least one of UW solution, William's E medium, or blood.

Another embodiment of the present technology includes a system for monitoring a biological tissue. The system includes a perfusion chamber, a heating element, a perfusion machine, a laser, a probe, a spectrometer, and a processor. The perfusion chamber holds the biological tissue. The heating element is in thermal communication with a perfusate. The heating element warms the perfusate. The perfusion machine is in fluid communication with the perfusion chamber. The perfusion machine pumps perfusate warmed by the heating element through the perfusion chamber. The laser generates an excitation beam. The probe is in optical communication with the laser and the biological tissue. The probe illuminates the biological tissue with the excitation beam and collects a resonance Raman signal emitted by the biological tissue in response to the excitation signal. The spectrometer is in optical communication with the probe. The spectrometer generates a Raman spectrum from the Raman signal. The processor is operably coupled to the spectrometer. The processor quantifies a reduced mitochondrial ratio of the biological tissue based on the Raman signal.

The biological tissue may be from an organ biopsy. The organ biopsy may be of a donor organ intended for transplant. The donor organ may be a liver, a heart, a kidney, or a lung. The processor may be configured to predict a probability of rejection of the organ by a patient based on the reduced mitochondrial ratio of the biological tissue.

The system may include a probe holder mechanically coupled to the probe. The probe holder may include an elastomeric probe cover to position the probe optics at a predetermined distance from the biological tissue. In one implementation, the predetermined distance may be about 5 mm to about 10 mm. In another implementation, the predetermined distance is about 0 mm.

Another embodiment of the present technology is a method of monitoring a biological tissue. The method includes perfusing the biological tissue with a perfusate, measuring a Raman spectrum of the perfusate after it circulates through the biological tissue, quantifying a concentration of cytochrome c in the perfusate from the Raman spectrum, and determining a viability of the biological tissue based on the concentration of cytochrome c in the perfusate.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally and/or structurally similar elements).

DETAILED DESCRIPTION

Figure 1:
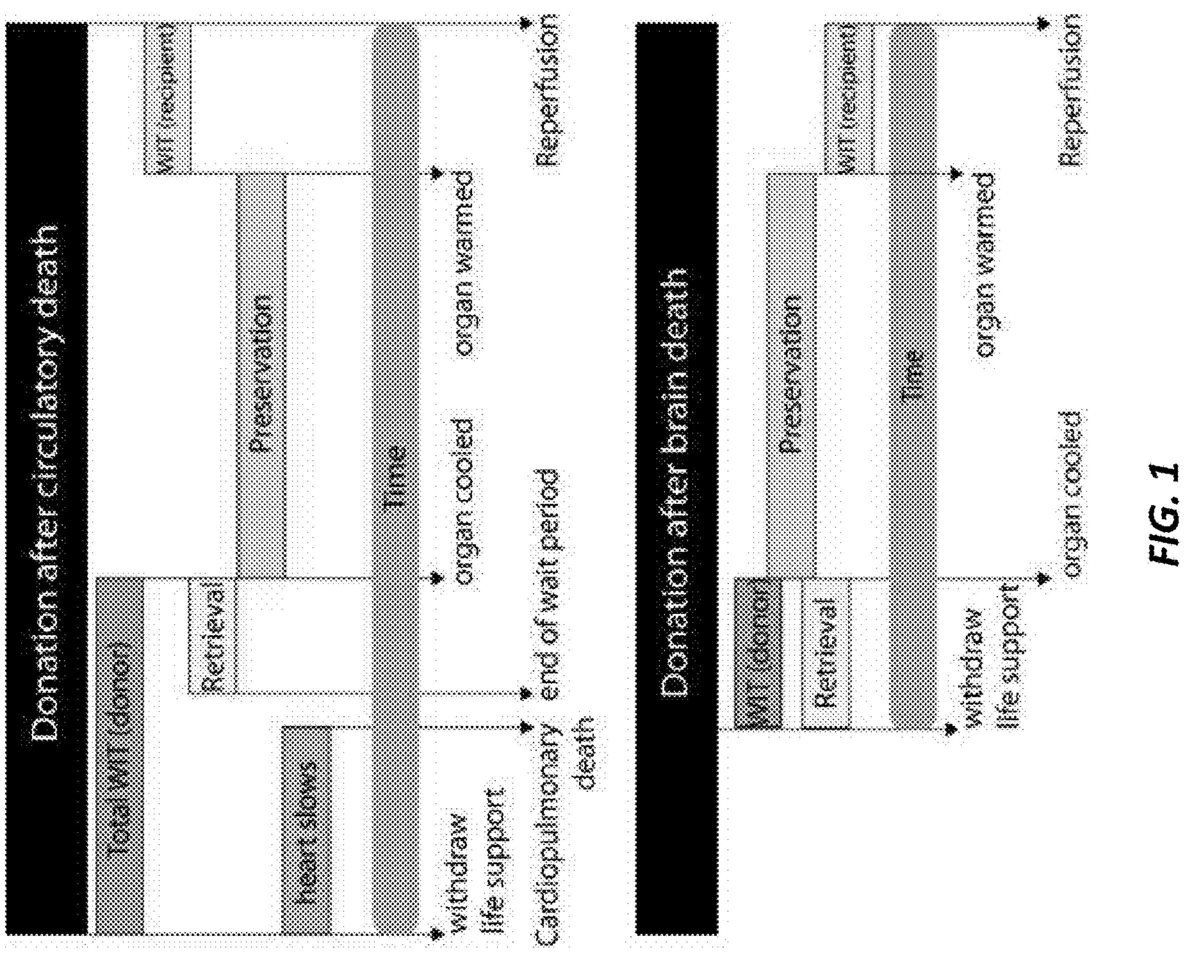
FIG. 1 is a timeline of the processes for organ donation following circulatory death (top) and brain death (bottom).

Current clinical standards for organ transportation and preservation call for static cold storage (SCS) at +4° C. Despite the unquestioned success of the SCS approach at curtailing ischemic injury incurred by organs during storage and at reperfusion, there are shortcomings. SCS precludes a thorough assessment of quality of the organ and is incompatible with compromised organs (e.g., DCD and steatotic grafts). Instead, clinicians are forced to use gross population-based donor risk statistics, such as age, race, height, cause of death, brain vs. cardiac death, full vs. partial graft transplantation, warm and cold ischemic time, and regional vs. national graft allocation to determine if a donor organ is viable. Because of such non-specific indicators coupled with the unacceptable costs of unsuccessful transplantations, perfectly good donor livers are discarded every year. Although several studies have attempted to remedy this problem, none have been translated into clinical practice.

An inventive resonance Raman spectroscopy (RRS) system enables clinicians to assess organ fitness safely and confidently prior to transplantation. This approach is compatible with current clinical standards of organ preservation and produces results rapidly in real-time. The RRS system can be used to measure resonance Raman reduced mitochondrial ratios (3RMR) in biological tissue. Measuring 3RMR can be used to quantify the amount of damage to a tissue for transplant caused by ischemia. This measurement can be used to determine the viability of the tissue for transplantation and predict transplant success.

In Raman spectroscopy, the wavelength of light from a narrowband laser is shifted to lower energy by a precise quantity determined by the frequency of the vibrational mode of the molecules it encounters. The wavelength shift (also called a Stokes shift) of inelastically scattered light can be separated from fluorescence to measure a redox state-specific spectral signature of a molecule. In the special case of RRS, the optically excited state overlaps a strong electronic absorption line, resulting in orders of magnitude enhancement of the Raman cross-section. Relevant to cellular energetics, the resonance Raman profiles of porphyrin structures (present in hemoglobin, myoglobin, and mitochondrial cytochromes) are amplified by 4 to 6 orders of magnitude (called an enhancement factor) when excited near the Soret absorption band (400 nm-450 nm). This enhancement makes the in vivo quantification of small quantities of such structures possible, even in a complex environment. Using this approach, the redox state of mitochondrial cytochromes in isolated mitochondria, in myocytes, and in bloodless tissues can be determined. In addition to determining mitochondrial cytochrome redox state, RRS can also be used to determine other mitochondrial breakdown products, as well as other tissue health indicators, such as tissue oxyhemoglobin saturation.

The RRS system can be used to quantify 3RMR and thereby quantify a mismatch between oxygen delivery and utilization. The redox state of the mitochondrial cytochrome active sites of electron flux within the electron transport chain (ETC) is spectroscopically quantifiable and varies based on the availability of oxygen. Deficient oxygen delivery, such as during ischemia, results in the progressive reduction of cytochromes. Cytochrome a,a3 in complex IV of the ETC is an ideal target for quantifying oxygen supply-demand relationships of the whole mitochondria because it is oxidized directly by molecular dioxygen and accounts for >95% of cellular oxygen utilization. In addition, cytochrome c is an ideal target for quantifying cellular damage that may be caused by extended periods of ischemia. Cytochrome c is normally associated with the inner membrane of the mitochondria. During ischemia, some amount of cytochrome c migrates to the outer membrane of the cell where it plays a role in membrane permeabilization and apoptosis. Changes in the protein structure of cytochrome c may indicate that a tissue has been damaged by ischemia. RRS provides a measure of both of these target cytochromes.

A problem with quantifying the viability of an organ for transplant using RRS is that both viable and non-viable organs may have similar RRS spectra upon initial removal from cold storage. To determine if an organ is healthy enough for transplantation, some or all of the organ can be perfused as a form of "stress test." Over a specified period in a perfusion chamber, viable and nonviable organs produce distinguishable changes in RRS spectra. The specified period of time may be 5 minutes, 15 minutes, 20 minutes, 30 minutes, 60 minutes, or 120 minutes. Preferably, the specified period is 30 minutes to 60 minutes.

It takes time for an organ or part of an organ to warm from a cooled state so that the metabolism increases toward normal. Once the metabolism is increased, the redox state in the non-viable tissue increases and the 3RMR decreases because there are fewer functional mitochondria to meet the energy demand. 3RMR may be measured continuously or at regular intervals (e.g., every 10 seconds, 30 seconds, 1 minute, 5 minutes, or 10 minutes) during the stress test. The 3RMR is calculated based on the ratio of reduced over total (reduced+oxidized) mitochondria, the values for which are determined using the regression algorithm in the device. In a viable tissue, the 3RMR may decrease below a threshold value when the organ or organ tissue is perfused and stay below this threshold value. In a non-viable tissue, the 3RMR may initially decrease and then rise above the threshold as the metabolic demand increases. A 3RMR value above the threshold after a specified period of time indicates non-viability. The 3RMR threshold value may be 5%, 10%, 15%, 20%, or 30%. Preferably, the 3RMR threshold value is 20%. The specified period of time may be 5 minutes, 15 minutes, 20 minutes, 30 minutes, 60 minutes, or 120 minutes. Preferably, the specified period is 30 minutes to 60 minutes. An initial decrease in 3RMR during perfusion may also be used to determine tissue viability. The changes in 3RMR over time or the slope of 3RMR over time as the tissue is warmed and perfused may also be used to determine tissue viability.

With increasing perfusion time, the 3RMR in the non-viable organ gradually rises, indicating that the functioning mitochondria in the non-viable organ are unable to meet the metabolic demand brought about by perfusion. The lack of functioning mitochondria may indicate tissue damage. In this way, the RRS system may determine the viability of organs for transplant. The RRS system can determine organ viability by collecting Raman spectra and measuring mitochondrial breakdown products in a whole organ, a tissue sample from an organ, the perfusate, or the hypothermic storage solution in which the organ is stored during SCS.

In one embodiment, serial RRS readings may be collected starting at the time of arrival and then every 1 hour for the first 12 hours and then every 6 hours up to 24 hours. Based on mouse studies using the RRS system, 24 hours of cold ischemia time may reveal near complete exhaustion of all metabolic substrates.

In order to replicate this "stress test" without removing the whole organ from SCS, the RRS system may instead take measurements of a tissue biopsy from the organ. While the organ remains stored in cold ischemia, the RRS system can take measurements from a perfused tissue biopsy from the organ. The RRS system may be configured to automatically perfuse and warm a small tissue sample taken via biopsy and collect continuous RRS measurements. This challenges the tissue in order to evaluate viability while the organ itself remains in cold ischemic storage. The RRS system warms and perfuses a tissue sample taken from the organ, and then monitors the 3RMR of the tissue sample over time. Perfusion challenges the tissue sample's mitochondria and can be used to determine organ viability. Temperature and oxygen supply to the tissue sample can be adjusted. In clinical practice, this "stress test" may provide a surgeon with key information prior to accepting or rejecting an organ for transplant.

The temperature of the tissue and the oxygen supply to the tissue are regulated by regulating the perfusate. In one embodiment, the perfusate is routed through a heat exchanger to warm it and regulate its temperature. In another embodiment, the perfusate is kept in a warmed reservoir. Either embodiment can be part of the RRS system or can be external components thermally coupled to the RRS system. The perfusate is oxygenated using an oxygenator. The oxygenator may be a membrane oxygenator with a thin, gas-permeable membrane separating the perfusate and gas flows.

In one embodiment, the system for measuring 3RMR comprises a portable, compact device housing a low power laser source and a high-resolution spectrometer. The laser power can be 4 mW-10 mW. The spectrometer can capture a range from 700 $cm^{-1}$-1700 $cm^{-1}$ with a full width at half maximum resolution (FWHM) of 8 $cm^{-1}$. The spectrometer has an internal real-time Stokes shift calibration reference (e.g., acetaminophen), and can produce an absolute Stokes shift accuracy of less than 0.4 $cm^{-1}$. The spectrometer is coupled to a small probe head via a flexible fiber optic bundle. The system can be used, for example, on a benchtop or mounted to a pole for ease of transport. A straightforward user interface located separately from the spectrometer itself operates on a computing device (e.g., tablet or laptop) and allows one-click operation of the spectrometer. Once the probe is positioned above the sample or organ, the user can just click a button on the user interface (e.g., "Start") to initiate the measurement. Values are recorded, displayed, and stored on the system. No additional calibration or adjustments are needed before collecting data. All spectral analysis can be performed by the system, which can display 3RMR results and trends to a user (e.g., a clinician) for immediate use in assessing organ damage. Spectra are saved on the system after every scan so that data can be reviewed or exported later using the user interface.

The system is easily used in the clinic and offers benefits including a small footprint, single-click operation, non-contact measurements, real time operation, and applicability to multiple organs (e.g., heart and kidneys). Livers are used here as an example organ that can be assessed using the 3RMR system. The 3RMR system may also be used to assess any tissue, biopsy, organelle, or cell culture that can be placed on a sample holder and analyzed using the system. Each tissue may use a unique cell design depending on the geometry of the sample and perfusion regulation needs. Examples of organs and/or organ tissue that can be assessed with the system include heart, kidney, pancreas, lung, and intestine.

The RRS system offers continuous multi-point monitoring of organs during machine perfusion. The RRS system can also be configured to measure spectra at certain time intervals. In this way, the system can be used to study the kinetics of 3RMR decay and cytochrome c release from mitochondria during ischemia and/or perfusion. The 3RMR changes in response to a stimulus (e.g., stopping perfusion, changing temperature, or adding something to the perfusate). Machine perfusion is used to maintain a steady state in which metabolic needs and supply are matched. Any changes in 3RMR over time during machine perfusion indicate a change in that balance (i.e., a change in metabolic needs). The kinetics of 3RMR decay, cytochrome c release, and release of mitochondrial breakdown products may be used as an indicator of organ viability.

As discussed in more detail in the Spectra Reference Library section below, spectra collected by the RRS system may be processed using a library of reference spectra. The library of reference spectra may include reference spectra for different types of tissues. It may also include specific spectra for mitochondrial cytochromes, including cytochrome a,a3 and cytochrome c, which are markers of mitochondrial redox state and mitochondrial ischemic damage.

Because a minimally invasive technique for quantifying viability could facilitate use of organs that would be discarded under current protocols, the RRS systems and techniques have the potential to significantly increase the number of organs available for transplant by verifying that those organs are viable for transplant. In some cases, organs or tissues may be perfused in a closed fashion where the perfusate flows through the organ's blood vessels. In other cases, organs or tissues may be perfused in an open fashion where at least part of the organ or tissue sample is immersed in perfusate, but the blood vessels are not directly perfused.

In each of the following embodiments, the RRS system may include one or more pressure sensors that provide feedback to regulate the pressure of the perfusate in the RRS system. A pressure sensor may be placed in the perfusate tubing prior to the organ or tissue to indicate inlet or perfusion pressure and after the organ or tissue to indicate any pressure drop across the organ or tissue. The pressure in the RRS system may be set so that it is high enough to ensure there is sufficient perfusate flow and low enough to preclude risking damage to the tissue. The pressure may be regulated by the pump (e.g., a roller pump, a peristaltic pump).

Perfusate flow may be regulated automatically based on pump settings to achieve a targeted pressure. For a whole organ, perfusion flow rates may be between about 100 mL/min to about 1000 mL/min, depending on the type of organ and the desired flow rate. For a smaller tissue sample, perfusion flow rates may be slower (e.g., about 1 mL/min to about 100 mL/min). Sensors may be used for continuous measurement of pressure on the inflow vessels. The targeted pressure may depend on the type of organ or tissue. For example, for heart perfusion, the target pressures may be 4-7 mmHg over the portal vein (with a flow rate of about 700 mL/min) and 50-80 mmHg on the artery (with a flow rate of about 200 mL/min). The perfusate may be oxygenated and buffered with a carbogen mixture of 95% $O_2$/5% $CO_2$, achieving maximum partial oxygen pressure of >700 mmHg and undepleted oxygen outflow (>200 mmHg).

Real time perfusate and blood measurements may be performed every 30 minutes and include pH, pO2, $HCO_3$, and lactate measured in the tissue (e.g., pulmonary vein, hepatic artery, or vena cava). Na, K, Ca, Cl, glucose, and hemoglobin may be measured in the perfusate reservoir.

The perfusate in the RRS system may be any fluid relevant to organ transplant storage or perfusion. The perfusate may be any prepared perfusate solution, whole blood, or a mixture of the two. The perfusate carries oxygen and nutrients to the organ or tissue. For example, the perfusate may be a cold storage solution (e.g., UW solution), saline, lactated Ringer's solution, dextrose solution, ABO-matched heparinized blood, Williams Medium E, or any combination of these fluids. The perfusate may include additives, including hydrocortisone, insulin, heparin, penicillin, or streptomycin. In one example, the perfusate is Williams Medium E (Sigma) supplemented with ABO-matched blood, hydrocortisone (10 mg/l), insulin (2 U/l), heparin (1000 U/l), penicillin (40,000 U/l) streptomycin (40 mg/l).

An organ or organ tissue sample in cold storage may be prepared for perfusion by flushing the organ or tissue sample with warm Lactated Ringers solution to clear the cold storage solution (e.g., UW solution). The organ or tissue sample may be connected to the perfusion system and heparinized blood perfusion may be started. The flow of perfusate and the concentration of oxygen in the perfusate are carefully controlled to prevent reperfusion injuries from exposing the tissue to too much oxygen too quickly. As an example, a liver may be perfused using approximately 2 L of perfusate.

RRS Measurements of Tissue During Tissue Sample Perfusion

The RRS system may be designed for automated measurements of tissue from liver biopsies. The RRS system may automate perfusion, warming, and redox measurements. Because warming an entire organ to collect viability measurements is not always practical, the RRS system can instead conduct measurements on biopsies. The RRS system allows consistent placement of a tissue sample, perfusion, warming, and rapid measurements.

Figure 2A:
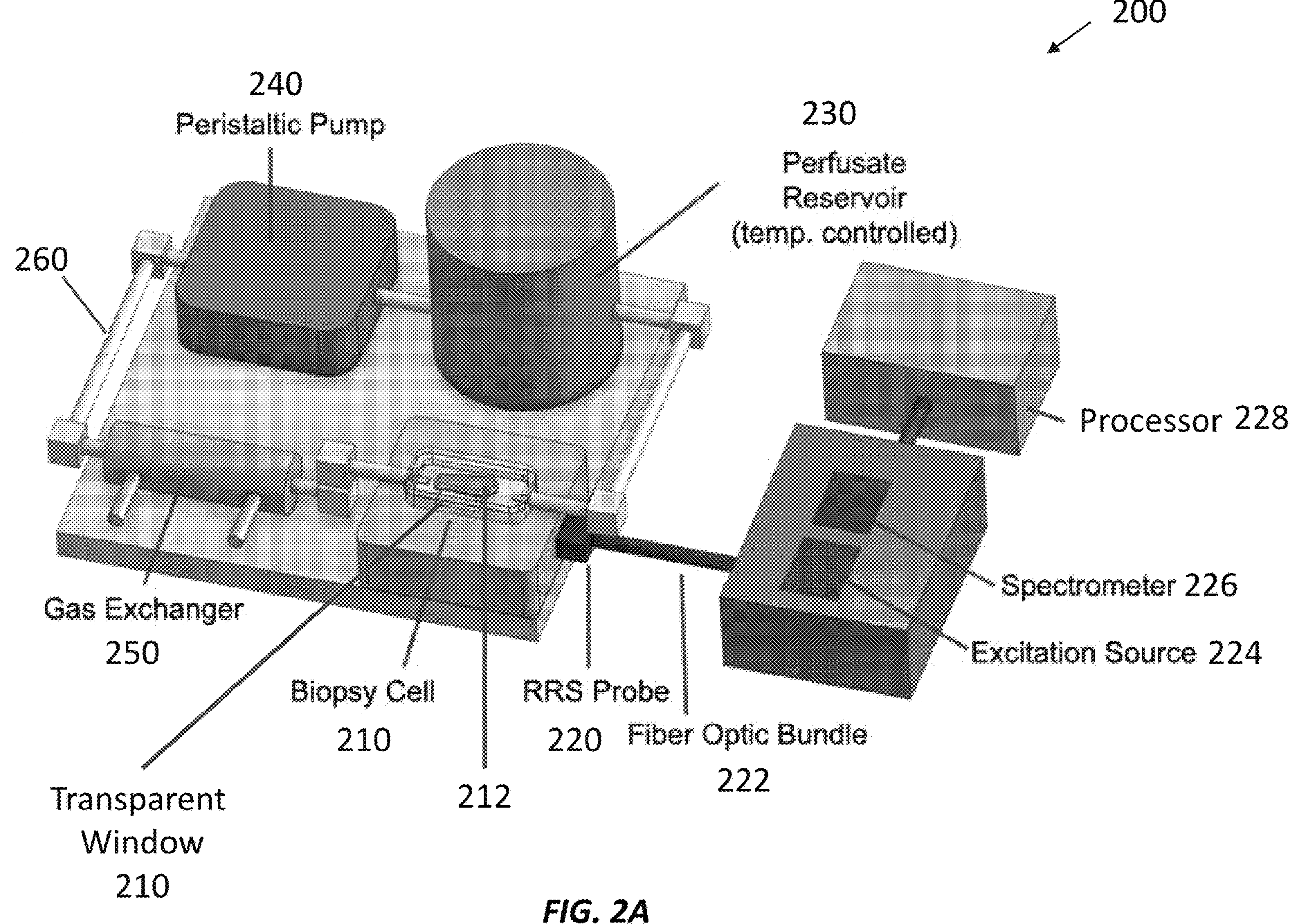
FIG. 2A is a diagram of an automated organ biopsy perfusion cell with a resonance Raman spectroscopy (RRS) probe.

FIG. 2A shows a diagram of an RRS system 200 that includes components to perfuse a small tissue sample 212. The RRS system includes a biopsy cell 210 to hold the tissue sample 212, an RRS probe 220, a MEMS rastering mirror, an excitation light source 224 (e.g., a diode laser), a spectrometer 226, and a processor 228. The tissue sample 212 sits on a transparent window 214 through which the RRS probe 220 transmits and collects light as explained below. The tissue sample 212 can be held in place with structures on the biopsy cell (not pictured) that secure it from above and below. The biopsy cell 210 may include glass, polymer, or metal components. The polymer components may be thermoplastics such as nylon or acrylonitrile butadiene styrene (ABS). The metal components may be corrosion-resistant metals, such as stainless steel or titanium.

The configuration and geometry of the structures holding the tissue sample in place in the biopsy cell depend on the tissue. In some cases, the tissue may rest on an oxygen permeable membrane to provide oxygen to the tissue. In other cases, the biopsy cell's holding structures may include a series of spikes that suspend the tissue in the middle of the flow. In other cases, there may be a circular clamping mechanism that holds two edges of the tissue while allowing perfusate to reach multiple sides of the tissue surface.

The biopsy cell may have different configurations and geometries. The biopsy cell may have a base which includes fluid channels to bring the perfusate to the biopsy chamber holding the tissue. There biopsy cell may include a second layer that seals the fluid channels and is secured in place with an adhesive and/or a clamping fixture. The biopsy cell has a window above the tissue that is fixed to the biopsy cell with an adhesive and/or a clamping fixture. The adhesive and/or clamping fixture prevent fluid leaking out around the window. The window provides optical access such that the RRS probe is optically coupled with the tissue. There is at least one inlet and outlet port for the perfusate to flow through the biopsy chamber in the biopsy cell. In some cases, the biopsy cell has multiple ports for sampling perfusate and/or adding other materials to the perfusate flow.

The window may be bonded to the cell with an adhesive or held in place with a clamping mechanism. The window may seal against the adjoining layer of the biopsy cell with or without a gasket such as an O-ring. The window is large enough to let the excitation beam (typically 1 mm-4 mm diameter) pass through it and to capture the returning scattered light. The window is at least about 5 mm in length. In some embodiments, the window is larger for larger tissues so that larger areas of the tissue may be scanned.

During perfusion of the tissue sample 212, perfusate from a perfusate reservoir 230 is circulated via perfusion tubing 260 through a pump 240 (e.g., a peristaltic pump or a roller pump), a gas exchanger 250, and the biopsy cell 210. The tissue sample 212 in the biopsy cell 210 is bathed in the circulating perfusate. The circulated perfusate may be directed back to the perfusate reservoir 230 for recirculation. The gas exchanger 250 sets the inlet oxygen pressure ($PO_2$) in the perfusate entering the biopsy cell 210. The gas exchanger 250 may be a membrane oxygenator. The gas exchanger 250 may provide oxygenation to the perfusate at a specified carbogen mixture (e.g., 95% $O_2$ and 5% $CO_2$) and a maximum partial oxygen pressure of >700 mmHg and undepleted oxygen outflow >200 mmHg. The perfusate may also circulate through a bubble trap (not shown) to capture and release gas bubbles from the perfusate so that the bubbles do not interfere with the Raman measurement.

Figure 2B:
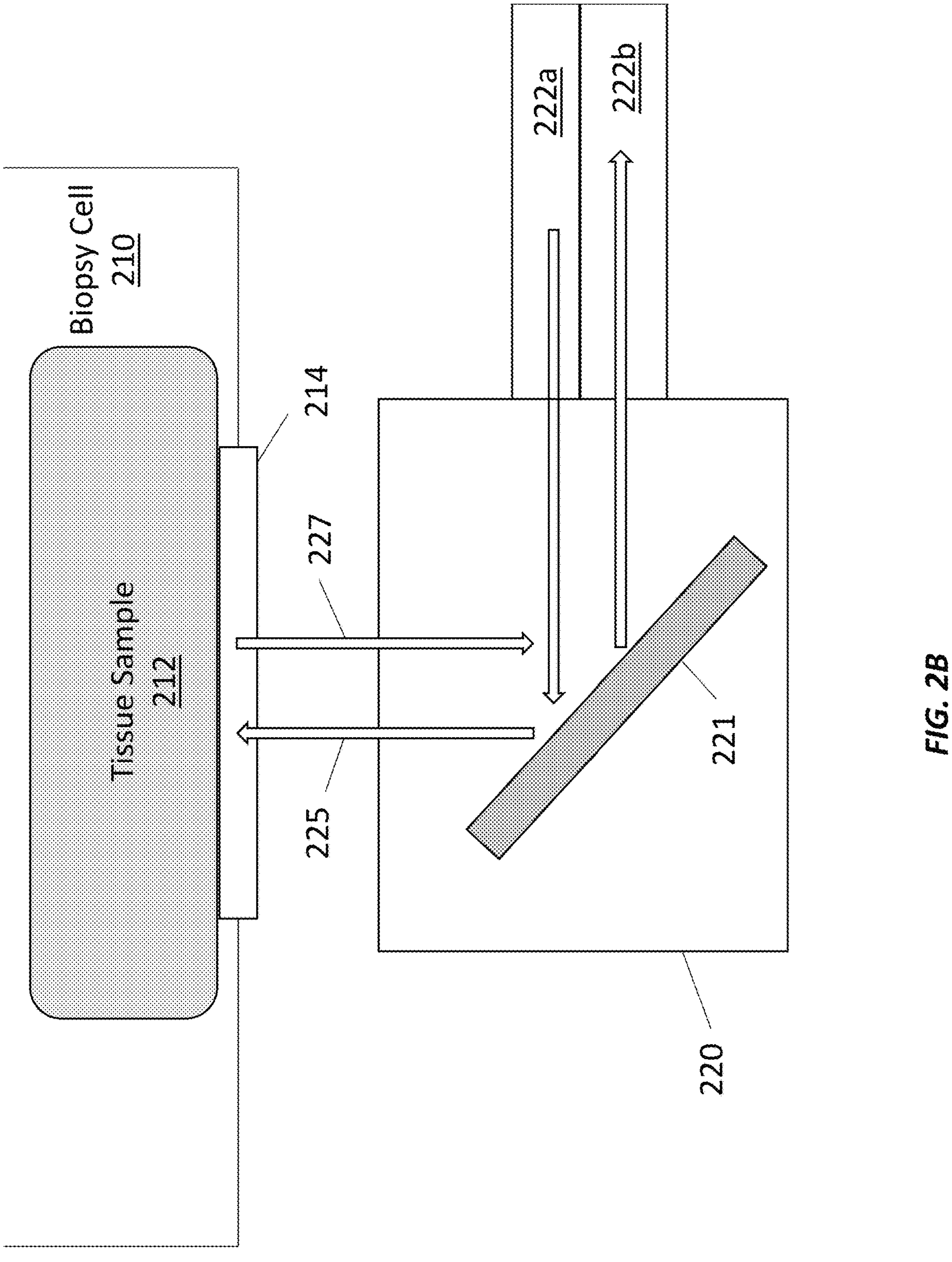
FIG. 2B is a diagram of the RRS probe in FIG. 2A.

FIG. 2B shows a cross-sectional diagram of the RRS probe 220 in the RRS system 200. The RRS probe 220 in the RRS system 200 is optically connected to the excitation light source 224 via a fiber optic cable or a bundle of fiber optic cables 222*a*. The RRS probe 220 is optically connected to the spectrometer 226 via a separate fiber optic cable or a bundle of multiple fiber optic cables 222*b*. A scanning MEMS mirror 221 directs a Raman pump beam or excitation beam 225 from the excitation light source 224 to the tissue sample 212 in the biopsy cell 210 via the transparent window 214. The MEMS mirror 221 can scan the excitation beam 225 in a one- or two-dimensional pattern, such as a raster-scanning pattern, across the surface of the tissue sample. Optics (not shown) may collimate the excitation beam 225 and/or focus it to a point in or on the sample 212. For example, a 9 mm diameter optic provides good radiometric collection efficiency and directs the excitation beam 225 onto/into the tissue sample 212 without causing discrete damage to the tissue sample 212. The optics and MEMS mirror 221 also couple the Raman signals 227 emitted by the tissue sample 212 in response to the excitation light 225 into the collection fiber(s) 222*b*, which guide the Raman signals 227 to the spectrometer 226. There may be a filter at either end of the collection fiber 222*b* to block or suppress light at the excitation wavelength and to pass or transmit light at the Raman wavelength(s). The spectrometer 226, which may be a grating spectrometer with a linear detector array, senses the intensity in each spectral bin with spectral resolution fine enough to distinguish features for 3RMR analysis.

The RRS probe 220 illuminates the tissue sample 212 and collects light from the tissue sample 212 through the transparent window 214 in the biopsy cell 210. FIG. 2B shows the RRS probe 220 disposed below or alongside the tissue sample 212 and using optics (e.g., a mirror) to direct light to and from the tissue sample 212. In another embodiment, the RRS probe 220 may be positioned with a straight line of sight to the tissue sample 212 for a simpler optical configuration. The transparent window 214 may be a material transparent to the relevant wavelengths of light, such as soda-lime glass, borosilicate glass, sapphire glass, or clear plastic that are transparent to the relevant wavelengths of light. In this example, the tissue sample 212 is positioned directly on top of the transparent window 214, with the RRS probe 220 mounted underneath the tissue sample 212 to illuminate the tissue sample 212 from below via the MEMS mirror 221. In other examples, the tissue sample 212 can be illuminated from the top or the side using an appropriate arrangement of optical fiber(s), mirrors, lenses, and/or other components. The RRS probe 220 may be supported on a mechanical arm.

Perfusate flows through the biopsy cell 210 to deliver oxygen and to warm the sample 212 before and/or while the RRS probe 220 collects Raman spectra from the sample 212. Perfusate is contained in a temperature-controlled reservoir 230 and pumped through the system with a pump 240. Oxygen may be supplied from a room oxygen supply to an inline gas exchanger, such as a membrane oxygenator. Temperatures and flow rates may be controlled by a program on a computer or smartphone (e.g., a Labview program on a connected laptop). Temperature sensors may be placed anywhere in the perfusate flow loop. Preferably temperature sensors are located in the perfusate reservoir. Pressure may be measured at the inlet to the biopsy cell. Perfusate flow rate may be controlled by the pump. In one embodiment, each of these systems has an independent, closed loop controller. In another embodiment, the output of the sensors is fed to an analog to digital converter connected to the computer operating the user interface via a wired (e.g., USB) or wireless (e.g., Bluetooth, Wi-Fi) connection.

The RRS probe may expose a constant 1.5 mm diameter spot to the excitation laser for a period of time. The period of time may be about 60 to about 180 seconds. Longer times provide a more stable measurement while shorter times provide more responsiveness to changes. The period of time may be chosen based on the signal strength from a particular tissue that provides sufficient signal with little residual after regression. The size of the spot may be about 1.5 mm to about 4 mm, depending on the size of the tissue to be analyzed. Larger spots provide a more generalized value while smaller spots provide targeted measurements of specific tissue structures.

The tissue sample 212 is collected from a whole organ. The tissue sample 212 may be collected using one of several methods for taking a tissue biopsy. The tissue sample 212 may be collected using a needle or a cutting tool. The tissue sample 212 should be large enough to have, represent, or mimic the structure of the organ but otherwise as small as possible. As an example, the tissue sample 212 may be collected from a donor organ using a large bore needle and may be about 2 millimeters in diameter and about 10 mm long. If the tissue sample is taken from an organ for donation, the size of the tissue sample is limited so that the organ function is not impaired, while still being large enough to maintain sufficient tissue structure to provide representative data. Tissue samples may also be collected by cutting with a scalpel or scissors. Biopsies may be taken from several sites (e.g., 3 or 4 sites) in the periphery and the core of the organ. This allows the comparison of readings at multiple sites and can be used to determine if there are differences between the periphery and the core of the organ.

The RRS system 200 can measure a series of Raman spectra from the tissue sample 212 during perfusion. The spectrometer 226 includes an electronics board that is connected to a processor 228. The processor 228 processes the Raman spectra from the spectrometer 226 and quantifies 3RMR in the tissue sample. The processor 228 receives Raman spectral data and processes it using a regression analysis and a reference library of reference Raman spectra stored in a non-volatile memory operably coupled to the processor 228. 3RMR data collected from the tissue sample during perfusion can be used to assess the viability of the donor organ from which the tissue sample was collected.

The system 200 can make RRS measurements continuously from the start of perfusion of the tissue sample 212. For example, the excitation light source 224 may be on and the spectrometer 226 may collect Raman spectra, e.g., at a rate of one spectrum per second. Alternatively, the system 200 can make RRS measurements intermittently, e.g., on demand or at defined time intervals. For example, 60 sequential spectra may be collected at a rate of one spectrum per second at certain time intervals, such as every 15 minutes.

The RRS system may perform normothermic machine perfusion (NMP) at 37° C. The perfusate reservoir 230 may include a temperature control system to control the temperature of the perfusate. The temperature of the tissue sample may be controlled by the temperature of the perfusate. The temperature of the biopsy cell may be controlled using a temperature control system to heat or cool the entire RRS system. Alternatively, the biopsy cell may be surrounded by and heated by a heating element. The perfusion tubing circulating the perfusate can also be surrounded by a heat exchanger to warm the perfusate before the perfusate reaches the tissue sample. The perfusate reservoir 230, the biopsy cell 210, and the perfusion tubing 260 may be surrounded by an insulation jacket to help control the temperature. The temperature of the tissue sample may be adjusted to a temperature in a range from about 4° C. to about 40° C. For example, the perfusate reservoir can be warmed to about 37° C. (body temperature), with the warmed perfusate warming the tissue sample during perfusion. The temperature of the tissue may be selected to tune the metabolic rate of the tissue. Colder temperatures may be used to slow down the metabolic rate and warmer temperatures may be used to increase the metabolic rate. Cold perfusate may also be used to extend storage times and/or gradually warm the organ prior to transplant.

RRS Measurements of an Organ During Organ Perfusion

The RRS system may be designed for automated measurements of an entire donor organ for transplant. The RRS system may automate perfusion, warming, and redox measurements during perfusion of the donor organ. The RRS system can be used to quantify how much damage an entire organ has.

Figure 3A:
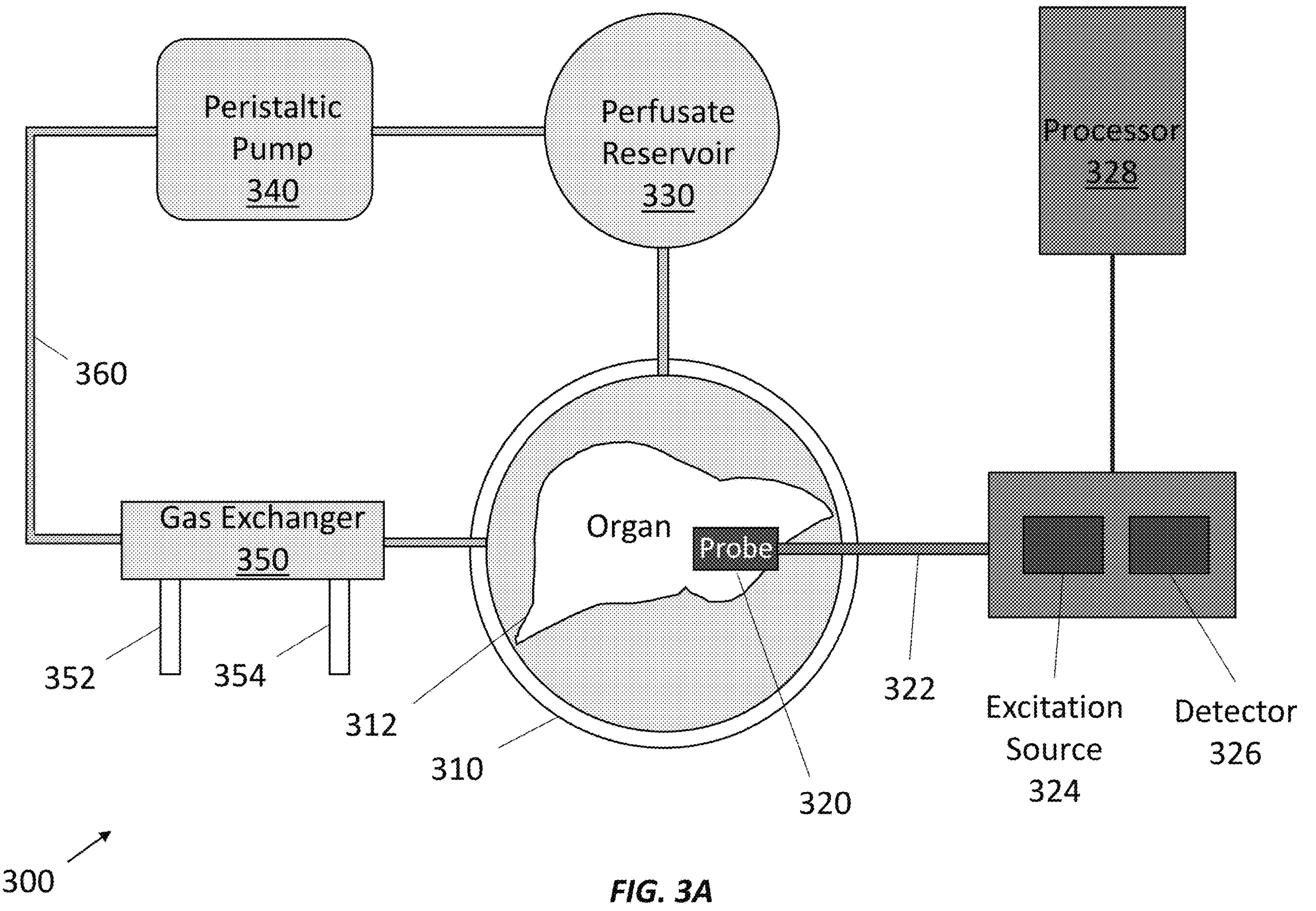
FIG. 3A is a diagram of an organ perfusion system with a RRS probe for measuring Raman signals from the organ.

FIG. 3A shows a diagram of a RRS system 300 for measuring Raman spectra from an organ during machine perfusion. The RRS system 300 includes an organ chamber 310 to hold a whole organ 312. The organ chamber is a closed chamber that holds fluid and maintains sterility. During perfusion, a pump 340 circulates perfusate in the RRS system 300 through a perfusate reservoir 330, a gas exchanger 350, and the organ chamber 310 via perfusion tubing 360. The gas exchanger 350 includes a gas inlet 352 and a gas outlet 354. The perfusate may also circulate through a bubble trap (not shown) to capture and release gas bubbles from the perfusate so that the bubbles do not interfere with the Raman measurement. The RRS system 300 includes a RRS probe 320 operably coupled to an excitation light source 324 (e.g., a laser) and a detector in a spectrometer 326, which may include a grating that diffract light at different wavelengths to different detector elements in a detector array. The excitation light source 324 and spectrometer 326 are operably coupled to a processor 328 that provides control of the excitation light source 324 and spectral analysis of spectral data from the spectrometer 326.

In one embodiment, perfusion tubing 360 may be fluidly coupled to blood vessels feeding the organ so that the organ is perfused through its blood vessels. One or more blood vessels may be fluidly coupled to the perfusion tubing 360 via sutures or clamps. In another embodiment, the organ is simply bathed in the perfusate circulating through the organ chamber 310.

The RRS probe 320 can be placed outside of the organ chamber 310 provided that the organ chamber is transparent to the relevant wavelengths of excitation light and RRS signal and/or has a window transparent to the relevant wavelengths of excitation light and RRS signal (e.g., glass or certain types of plastic). For example, the organ chamber may be a transparent plastic bag, similar to a blood storage bag. The probe is positioned about 10 mm away from the organ surface and can be mechanically scanned to cover a larger area of the organ or to move to various substructures on the organ.

Figure 3B:
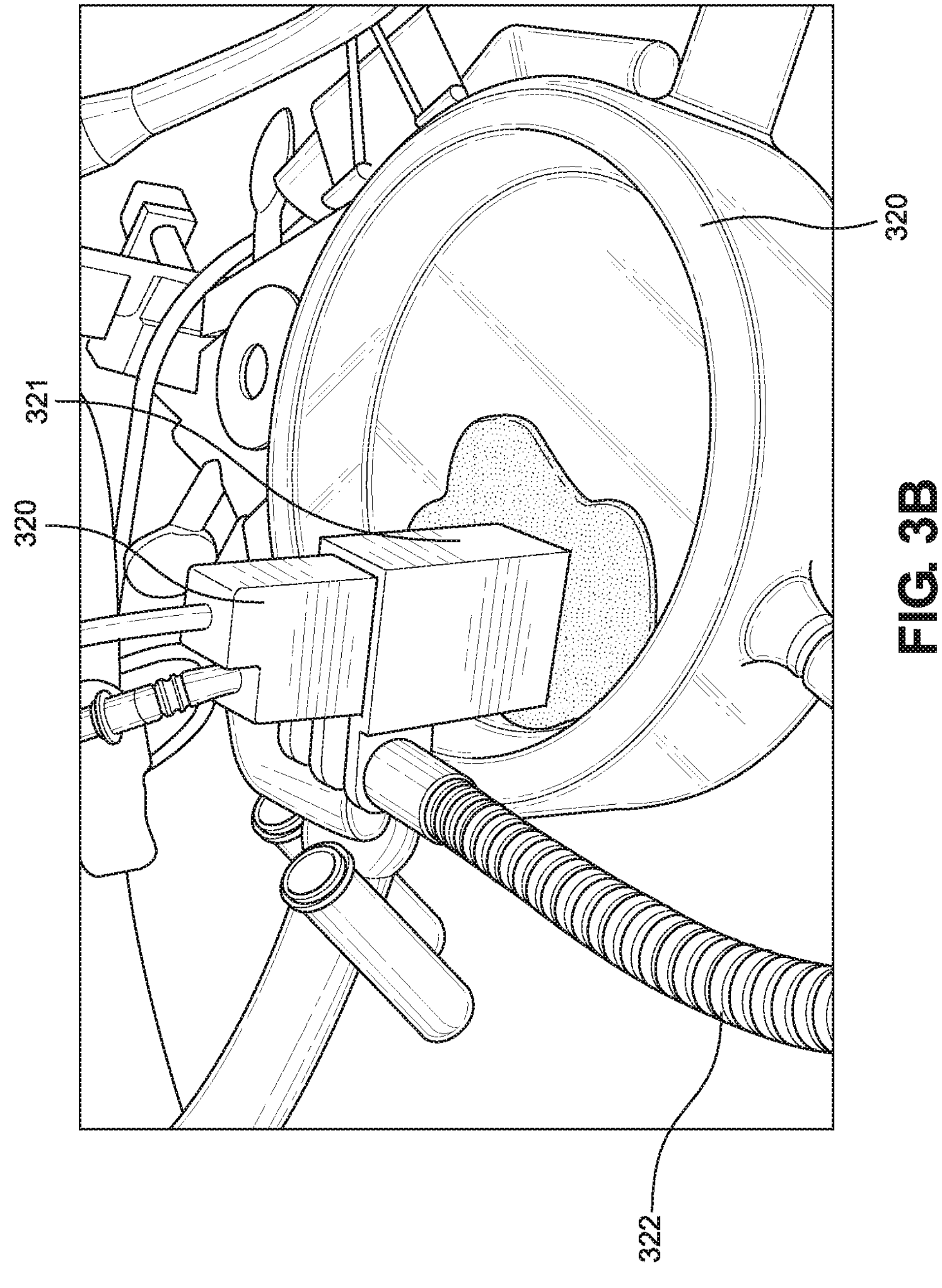
FIG. 3B is a picture of the RRS probe and probe holder in FIG. 3A.
Figure 3C:
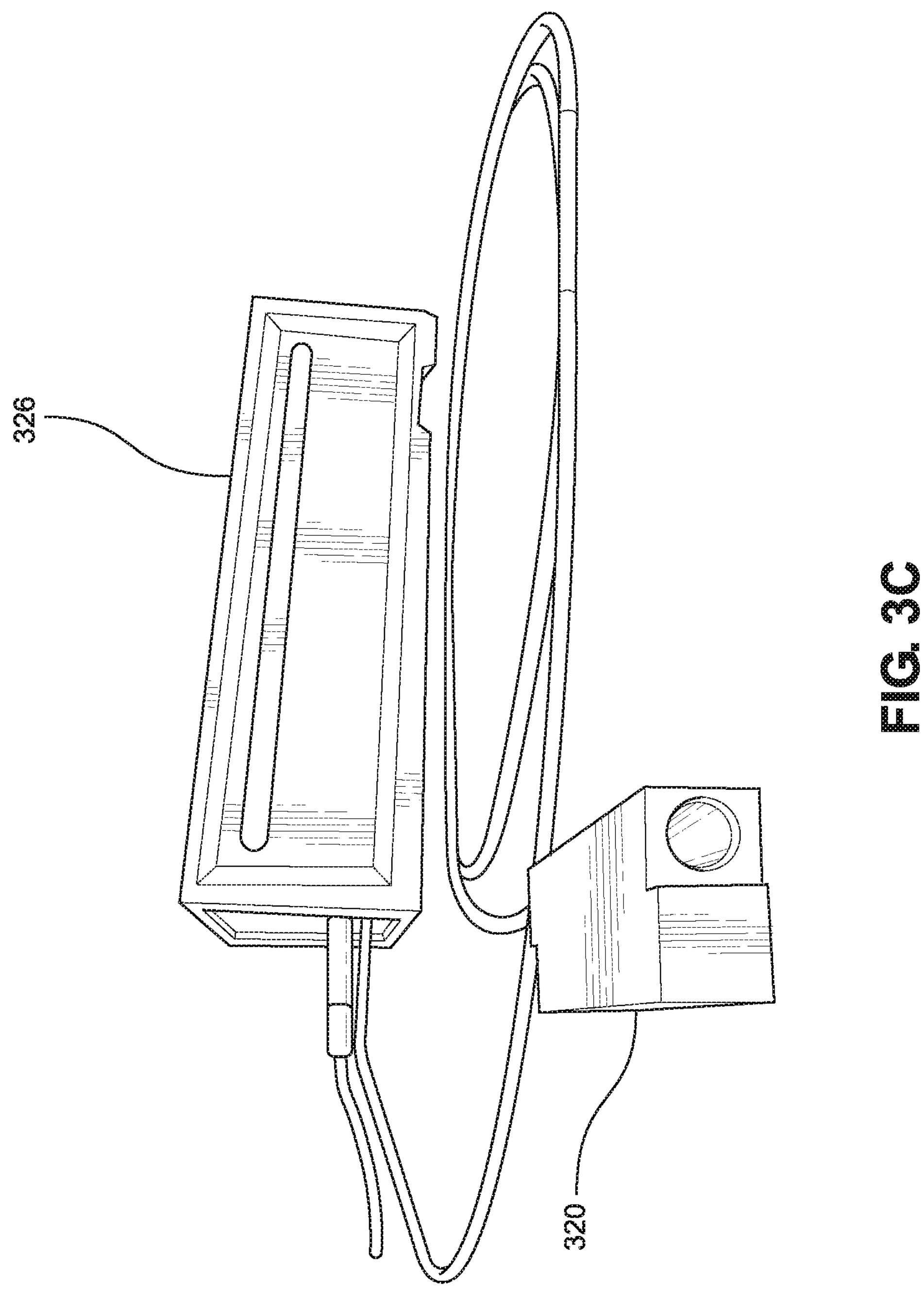
FIG. 3C is another picture of the RRS probe in FIG. 3A.

FIGS. 3B and 3C show the RRS probe 320 and spectrometer 326. The excitation light may be in the visible spectrum. The excitation light may have a wavelength of about 400 nm to about 480 nm. For example, the RRS system may use a 405 nm, 420 nm, 430 nm, or 441 nm excitation source. The spot size of the excitation light is about 1.5 mm to about 4 mm in diameter.

The probe in the RRS system may be in direct contact with the surface of the biological tissue. It can also make standoff measurements from some distance above, below, or to the side of the organ. Non-contact readings may be taken from several sites throughout the organ (e.g., about 5 to about 20 sites). FIG. 3B shows the RRS probe 320 and a probe holder 321 of the RRS system in FIG. 3A. The probe holder may enable the RRS probe to be about 0 mm to about 10 mm away from the tissue surface. For example, the probe holder includes an elastomeric probe cover that enables accurate stand-off positioning of the probe optics about 10 mm from the tissue surface while blocking environmental light. The probe holder 321 is adapted to be compatible with a variety of different arms in order to accurately position the probe 320 and hold it in place during measurements.

If the tissue is exposed, the probe may be in contact with the tissue (i.e., 0 mm away from the tissue surface). Measurements with the probe contacting the tissue may reduce noise from environmental light and assures that all scattered light reaches the probe. If the tissue is inside of the organ chamber (for example, to maintain sterility), then the probe can be disposed away from the tissue surface and outside of the organ chamber. The probe optics may be configured differently for contacting the tissue surface or being disposed away from the tissue surface. Also, contact with the tissue may affect the function of the tissue.

The processor 326 can be used to control the excitation light source power, the range of the spectrum included in the measurement, and the chromophores to be included in the reference library used to analyze the RRS data. An excitation light source power of about 1 mW to about 10 mW may be used in the RRS system.

In some cases, the RRS system for whole organ measurement includes two independent perfusate circulation loops. Each loop may include a pump (e.g., a roller pump, a peristaltic pump), hollow-fiber oxygenator and a bubble trap. This setup may be particularly suited for certain organs. For example, for heart perfusion, two independent perfusate loops may be used for separate portal and arterial perfusion.

Figure 3D:
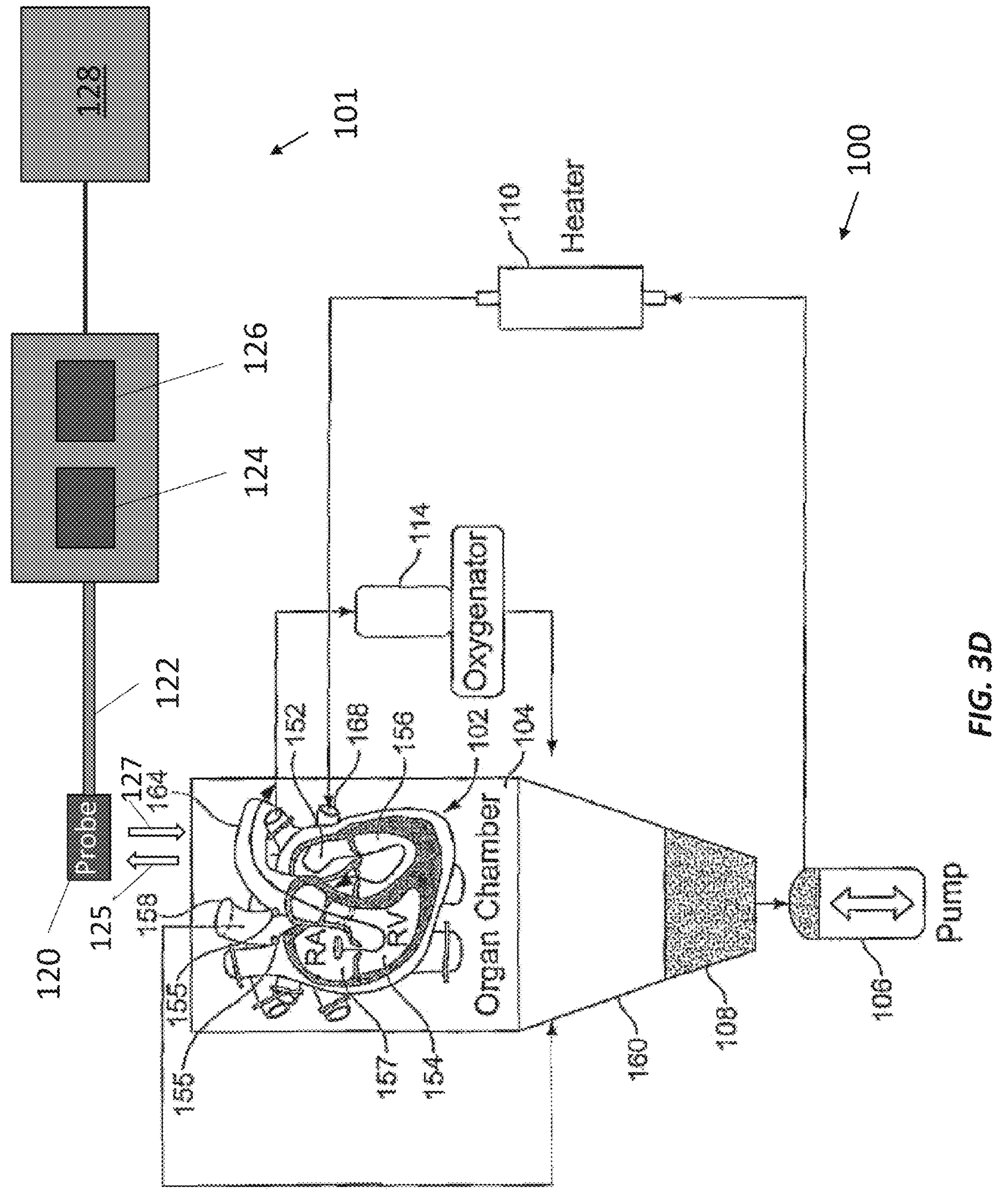
FIG. 3D is another embodiment of an organ perfusion cell with a RRS probe for measuring Raman signals from the organ.

FIG. 3D shows an embodiment of an RRS system 101 for measurement of a whole heart during machine perfusion. In this embodiment, the RRS system 101 is integrated with a commercially available organ perfusion system 100. The perfusion system 100 circulates the perfusate 108 to the heart 201 in the same manner as blood would circulate in the human body. The perfusate enters the left atrium 152 of the heart 102 via the pulmonary vein 168. The perfusate 108 flows away from the right ventricle 154 via the pulmonary artery 164 and away from the left ventricle 156 via the aorta 158. The perfusion system 100 may pump perfusate to the heart at a near physiological rate of between 1 L/min and about 5 L/min.

The perfusate 108 is loaded into the reservoir 160. The pump 106 pumps the perfusate 108 from the reservoir 160 to the heater assembly 110. The heater assembly 110 heats the perfusion fluid 108 to or near a normal physiological temperature (e.g., about 32° C. to about 37° C.). From the heater assembly 110, the perfusate 108 flows to the organ chamber assembly 104 via an interface that includes cannulation to vascular tissue. The heart 102 expels perfusate 108 through the left ventricle 156 via an interface and through the right ventricle 154 via a pulmonary artery interface. The perfusate flows from the pulmonary artery interface into a gas exchanger 114 where the perfusate is re-oxygenated. The perfusate 108 returns to the reservoir 160 following re-oxygenation.

The RRS system 101 includes a RRS probe 120 operably coupled to an excitation light source 124 (e.g., a laser) and a detector 126 via separated optical cables 122. The excitation light source 124 and detector 126 are operably coupled to a processor 128 that provides control of the excitation light source 124 and provides spectral analysis of spectral data from the detector 126. The RRS probe 120 provides excitation light 125 to a portion of the heart 102 and detects Raman signals 127 from the heart 102.

The perfusate 108 flows through the valves of the heart. This flow does not affect the RRS measurements. For heart perfusion, either the coronary sinus (in the right atrium) or the coronary arteries (in the aorta) are cannulated so that the perfusate 108 perfusates the smaller blood vessels that feed the heart itself. The heart is unique in that it pumps blood through the main chambers, but also perfuses its own vasculature to feed the myocardium.

Figure 4:
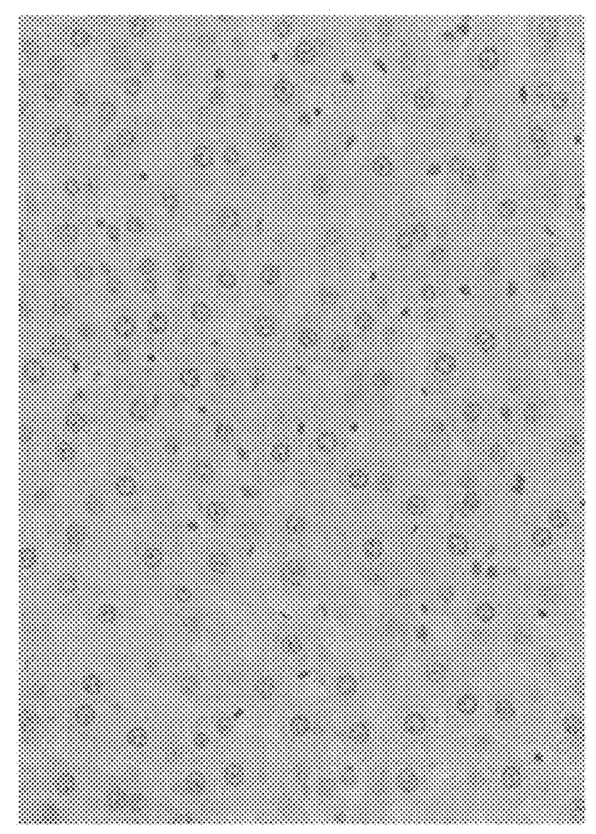
FIG. 4 is a histology image of liver tissue after exposure to laser light from the resonance Raman spectroscopy probe.

FIG. 4 shows the results of a test of the safety of an excitation light source used in the RRS systems. The RRS systems may use a laser excitation source similar to a typical laser pointer. For example, it can have a 4 mW laser power and a 2 mm2 laser spot size. The laser excitation source may be classified as Class I, meaning there is no skin hazard according to the ANSI laser safety standards. Because the laser is only activated when in contact with the tissue and covered such that laser light is not visible, there is no ocular hazard. To confirm the laser safety, a rat liver tissue was subjected to a 10 mW laser for repeated 60 second exposures and then samples were collected for histological analysis. No tissue damage was observed.

RRS Measurements of Perfusate During Tissue Sample Perfusion

The RRS system may be designed for automated measurements of perfusate during machine perfusion of an organ or tissue sample. The RRS system may automate perfusion, warming, and redox measurements. Sensitivity and specificity analysis of the Raman spectra can be used to determine a threshold cutoff for viability of the organ based on Raman spectra from the perfusate.

The RRS probe may be used to measure Raman signals from perfusate in a variety of configurations. In one configuration, the RRS probe may be optically coupled to a microfluidic channel fluidically coupled to the perfusion tubing. In another configuration, the RRS probe may be optically coupled to the perfusion tubing itself. In another configuration, samples of perfusate may be collected from a perfusion system (e.g., by the same port used to collect perfusate for gas, pH, and transaminase measurements). In this configuration, perfusate samples may be drawn using a syringe from a port in the perfusion tubing. Perfusate samples are then analyzed using the RRS probe. In this configuration, the RRS probe may be located remotely from the perfusion system.

Figure 5A:
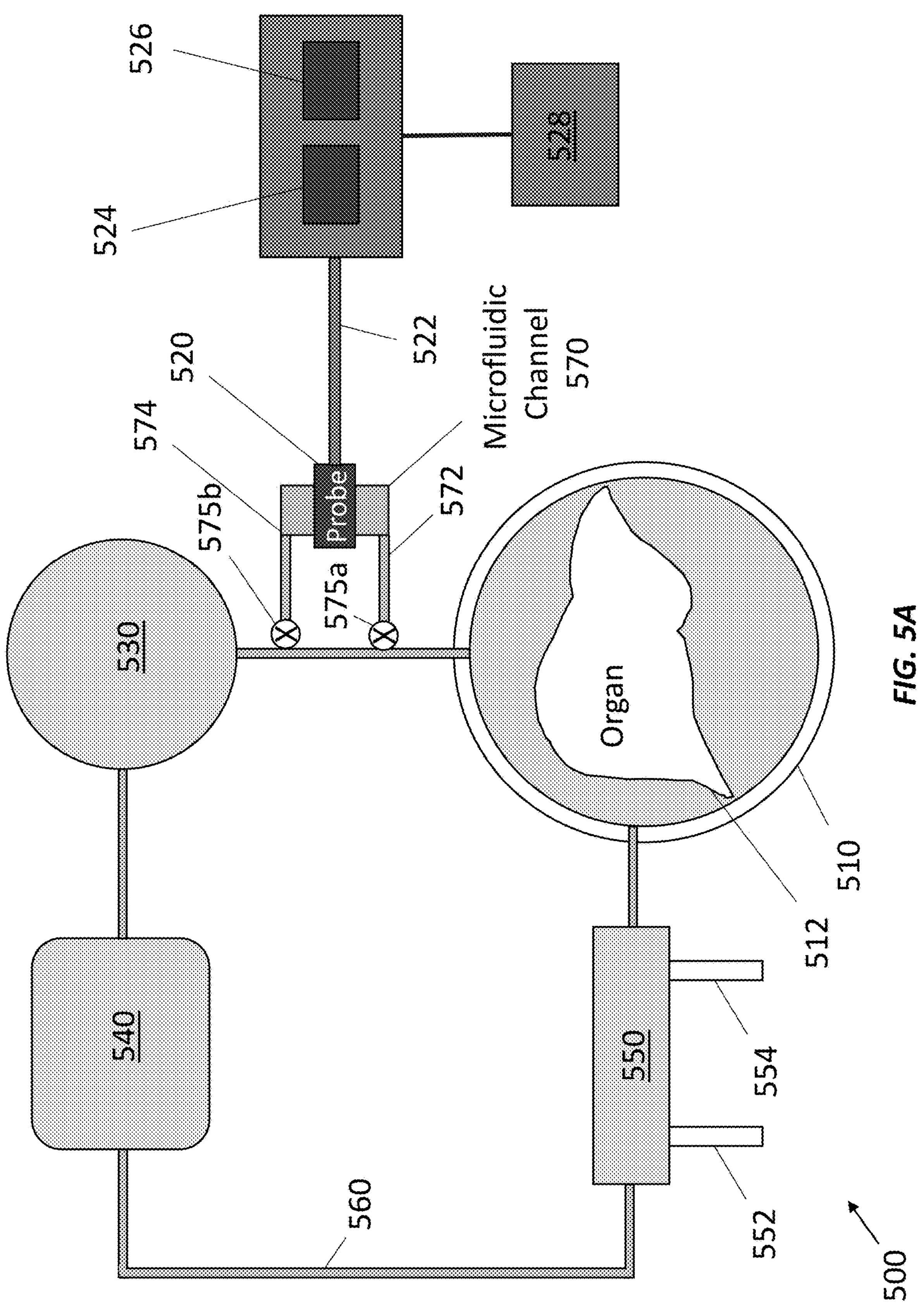
FIG. 5A is a diagram of a perfusion cell with a microfluidic channel and RRS probe for measuring Raman signals from perfusate.

FIG. 5A shows a diagram of a RRS system 500 for measurement of perfusate during machine perfusion of whole organ or tissue sample 512. The RRS system 500 includes an organ chamber or tissue sample holder 510. During perfusion, perfusate circulates in the RRS system 500 through a perfusate reservoir 530, a pump 540, a gas exchanger 550, and the organ chamber or tissue sample holder 510 via perfusion tubing 560. Before returning to the perfusate reservoir 530 and after leaving the organ chamber or tissue sample holder 510, at least some of the perfusate circulates through a microfluidic channel 570 via an inlet 572 and an outlet 574. Valves 575*a* and 575*b* at the inlet 572 and the outlet 574 may be operated to control flow through the microfluidic channel 570. The RRS probe 520 is operably coupled to an excitation light source 524 (e.g., a laser) and a detector in the spectrometer 526. The excitation light source 524 and detector 526 are operably coupled to a processor 528 that provides control of the excitation light source 524 and provides analysis of spectral data from the detector 526.

Figure 5B:
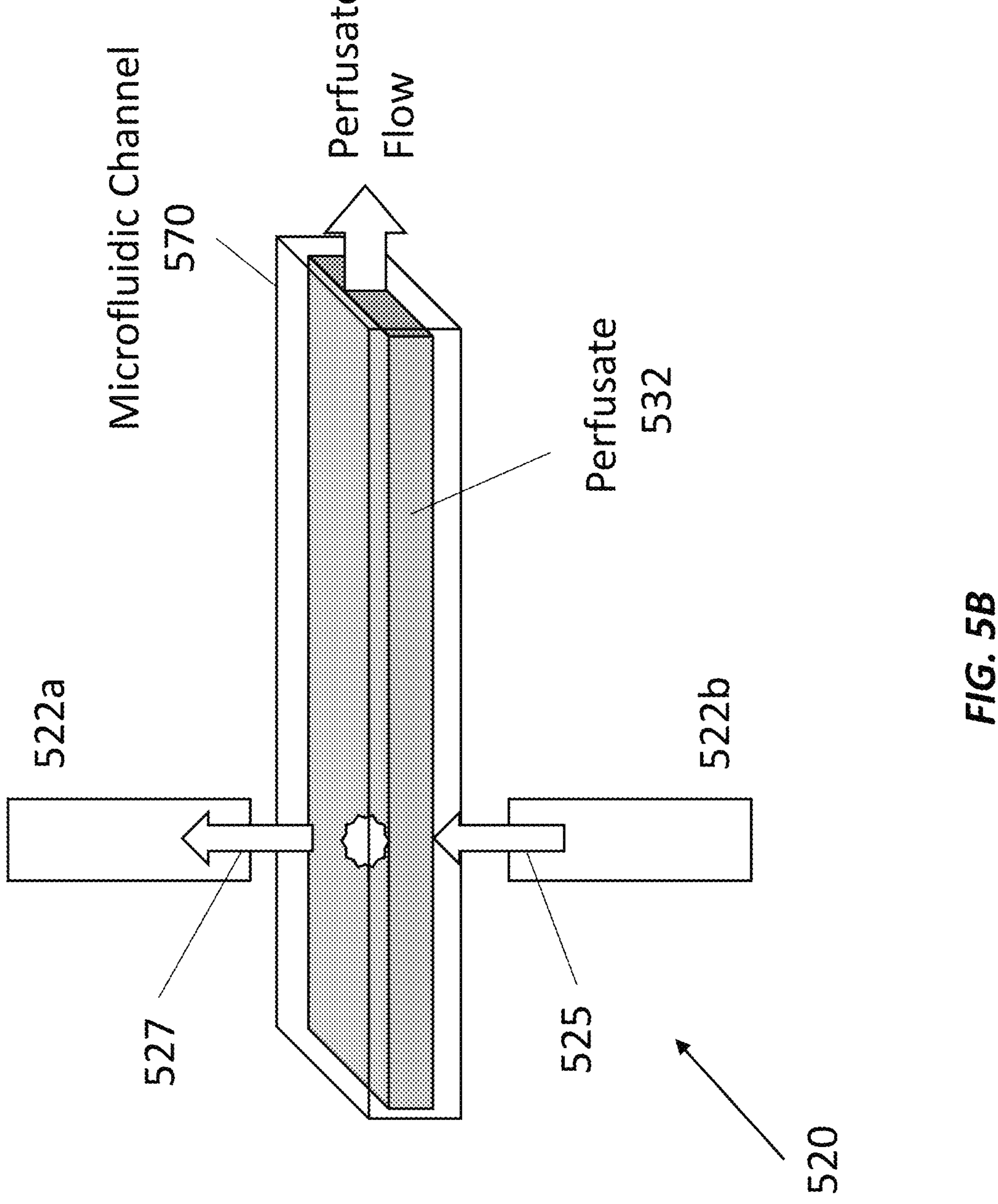
FIG. 5B is a diagram of the RRS probe and microfluidic channel in FIG. 5A.

FIG. 5B shows a cross-sectional diagram of the RRS probe 520 in the RRS system 500. A first optical fiber or fiber-optic bundle 522*a* is butted against the microfluidic channel 570, which is transparent at the excitation and Raman wavelengths, and guides a Raman pump beam 525 from the excitation light source 524 to the microfluidic channel 570. The Raman pump beam 525 illuminates the perfusate 532, producing Raman light 527 that radiates isotropically. A second optical fiber or fiber-optic bundle 522*b* couples a portion of the Raman light 527 from the perfusate 532 to the spectrometer 526 for detection.

The microfluidic channel 570 provides a known volume of perfusate for precise concentration measurements by the RRS probe 520. The microfluidic channel 570 is a section of tubing that defines a wider and thinner channel so that the RRS probe measures RRS signals through a known, shallow thickness of the perfusate fluid stream. Since the sample volume under the probe is known, concentrations can be calculated based on the signal strength.

Figure 6A:
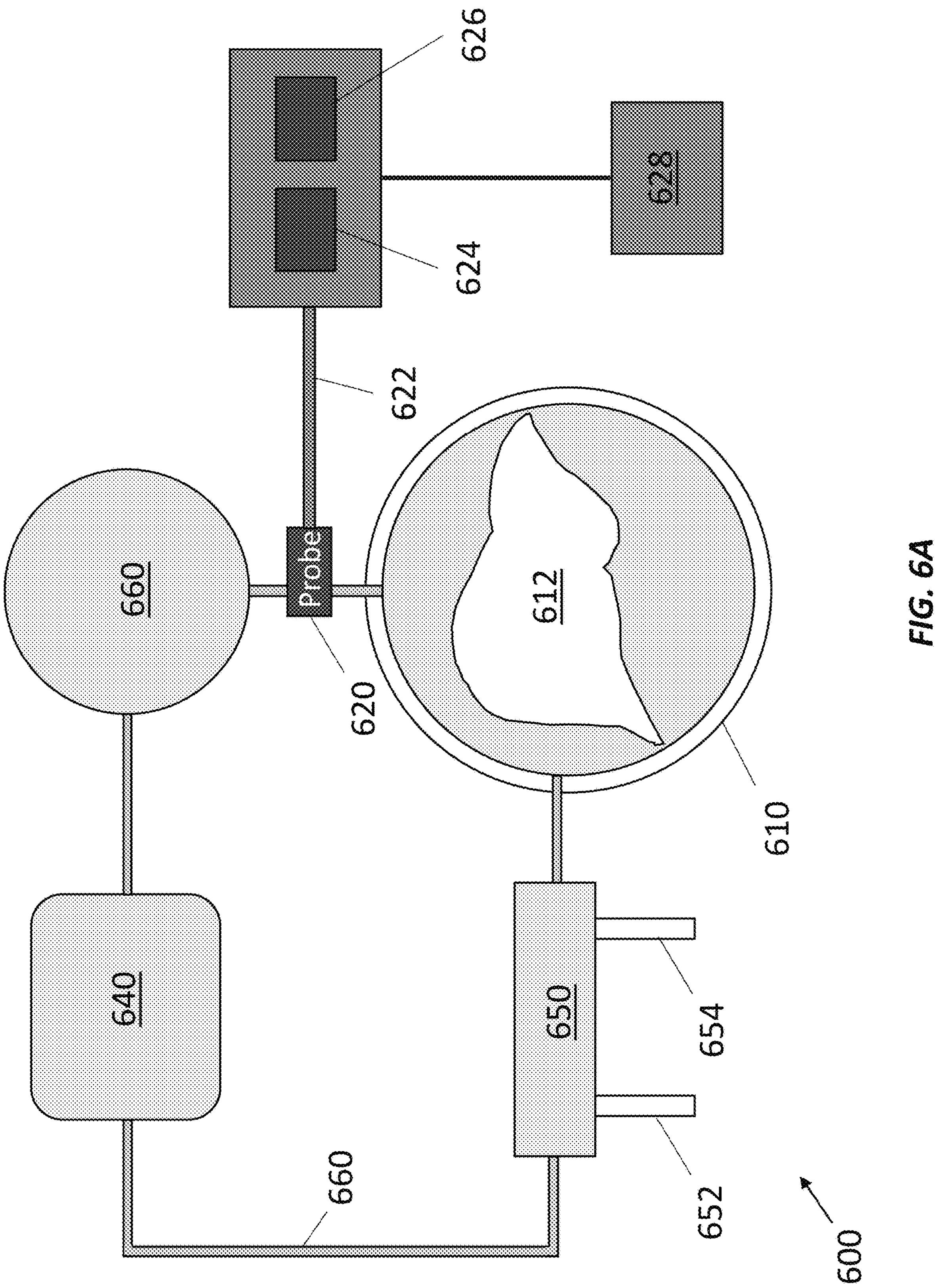
FIG. 6A is a diagram of a perfusion cell with an RRS probe for measuring Raman signals from perfusate.

FIG. 6A shows a diagram of a RRS system 600 for measuring Raman signals from perfusate during machine perfusion of a whole organ or tissue sample 612. The RRS system 600 includes an organ chamber or tissue sample holder 610. During perfusion, perfusate circulates in the RRS system 600 through a perfusate reservoir 630, a pump 640, a gas exchanger 650, and the organ chamber or tissue sample holder 610 via perfusion tubing 660. After leaving the organ chamber or tissue sample holder 610, the RRS probe 620 takes RRS measurements of the perfusate in the tubing 660. The RRS probe 620 is operably coupled to an excitation light source 624 (e.g., a laser) and a detector in the spectrometer 626. The excitation light source 624 and detector 626 are operably coupled to a processor 628 that provides control of the excitation light source 624 and provides analysis of spectral data from the detector 626.

Figure 6B:
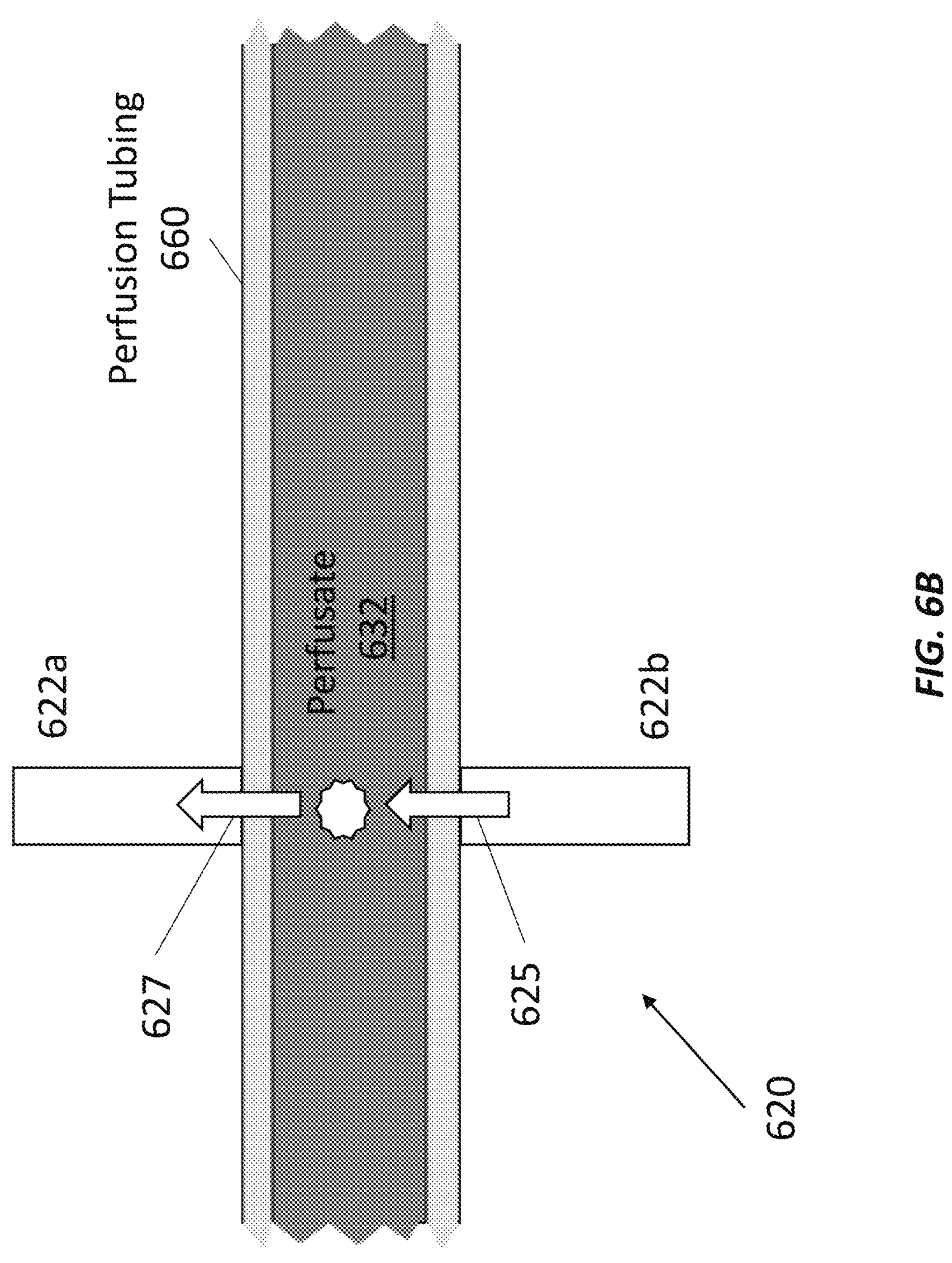
FIG. 6B is a diagram of the RRS probe and perfusate tubing in FIG. 6B.

FIG. 6B shows a cross-sectional diagram of the RRS probe 620 in the RRS system 600. A first optical fiber or fiber-optic bundle 622*a* is butted against the perfusion tubing 660, which is transparent at the excitation and Raman wavelengths, and guides a Raman pump beam 625 from the excitation light source 624 to the perfusion tubing 660. The Raman pump beam 625 illuminates the perfusate 632, producing Raman light 627 that radiates isotropically. A second optical fiber or fiber-optic bundle 622*b* couples a portion of the Raman light 627 from the perfusate 632 to the spectrometer 626 for detection.

Hypothermic storage solution in which an organ is stored may be analyzed in a similar way to that used to analyze the perfusate. A sample of the hypothermic storage solution may be taken from the bag or vessel in which the organ is stored. The sample is put in a vial and the vial is placed in front of the RRS probe. Breakdown products in the storage solution are seen as new peaks in the RRS spectrum as compared to the fresh hypothermic storage solution.

Spectral Reference Library

Figure 7:
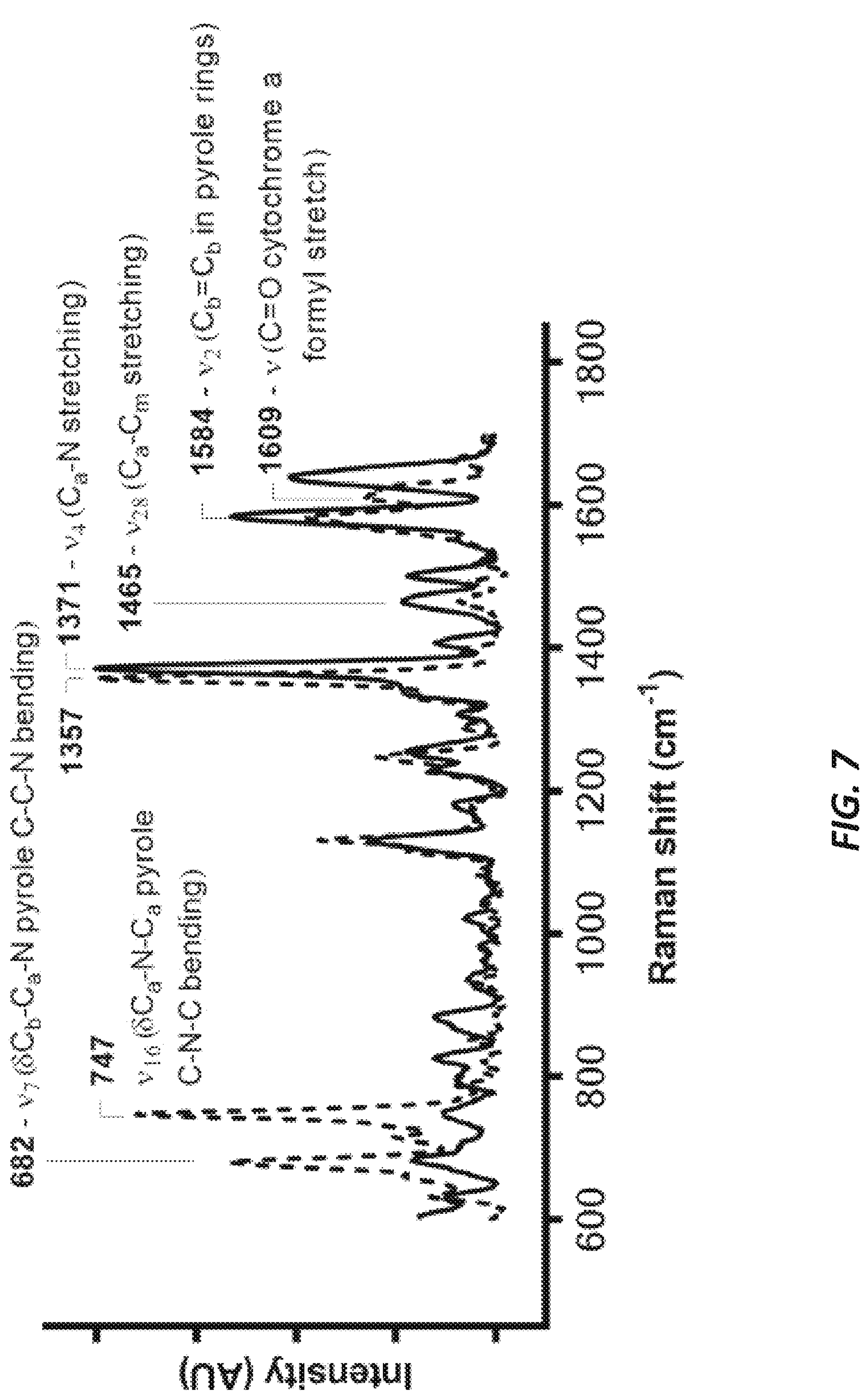
FIG. 7 is a graph of resonance Raman spectra of oxidized and reduced mitochondria used as part of a reference library for regression analysis of resonance Raman spectra collected with an RRS probe.
Figure 8:
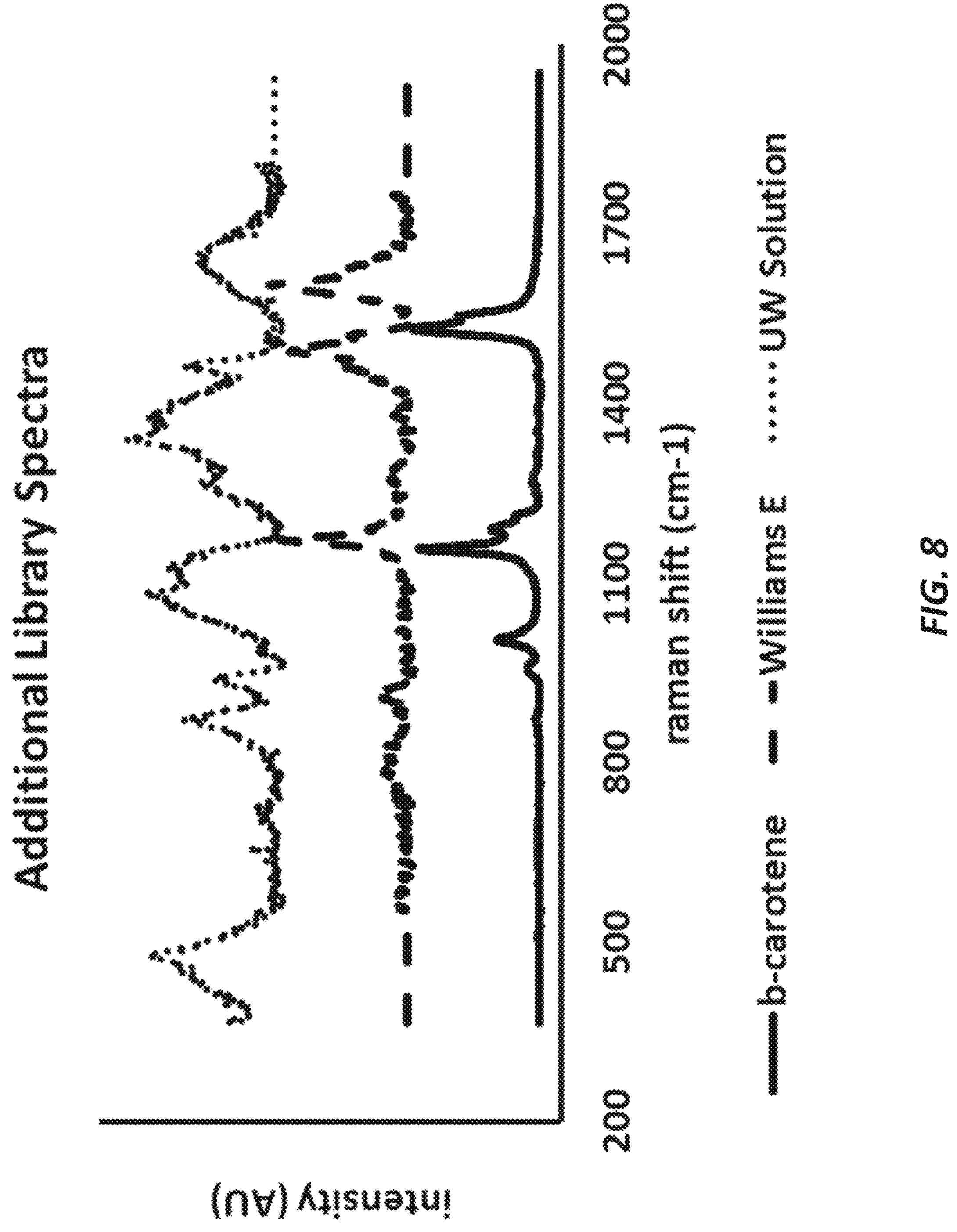
FIG. 8 is a graph of resonance Raman spectra of beta carotene, Williams E medium, and UW solution used as part of a reference library for regression analysis of resonance Raman spectra collected with an RRS probe.

A spectral reference library is developed and used using the RRS system. FIG. 7 shows examples of reference spectra collected for a reference library showing oxidized and reduced mitochondria spectra. FIG. 8 shows additional examples of reference spectra collected for a reference library showing beta carotene, UW solution, and Williams E perfusate spectra. These chromophore spectra may be included in the regression analysis of spectral data processed by the processor for 3RMR determination in order to account for their Raman peaks in the measured Raman spectra.

Figure 9A:
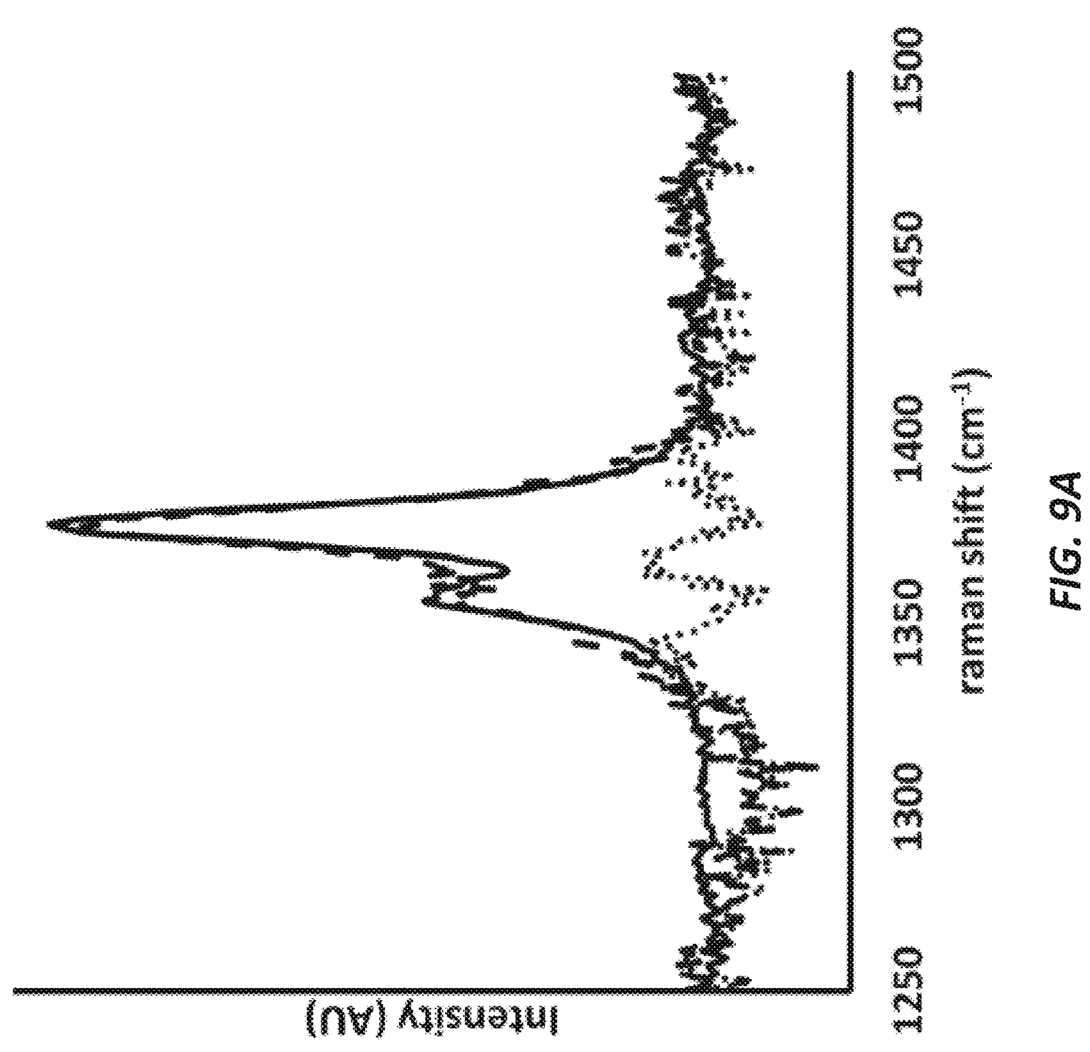
FIG. 9A is a graph of a resonance Raman spectrum from a blood perfused human liver analyzed with only hemoglobin in the regression library.
Figure 9B:
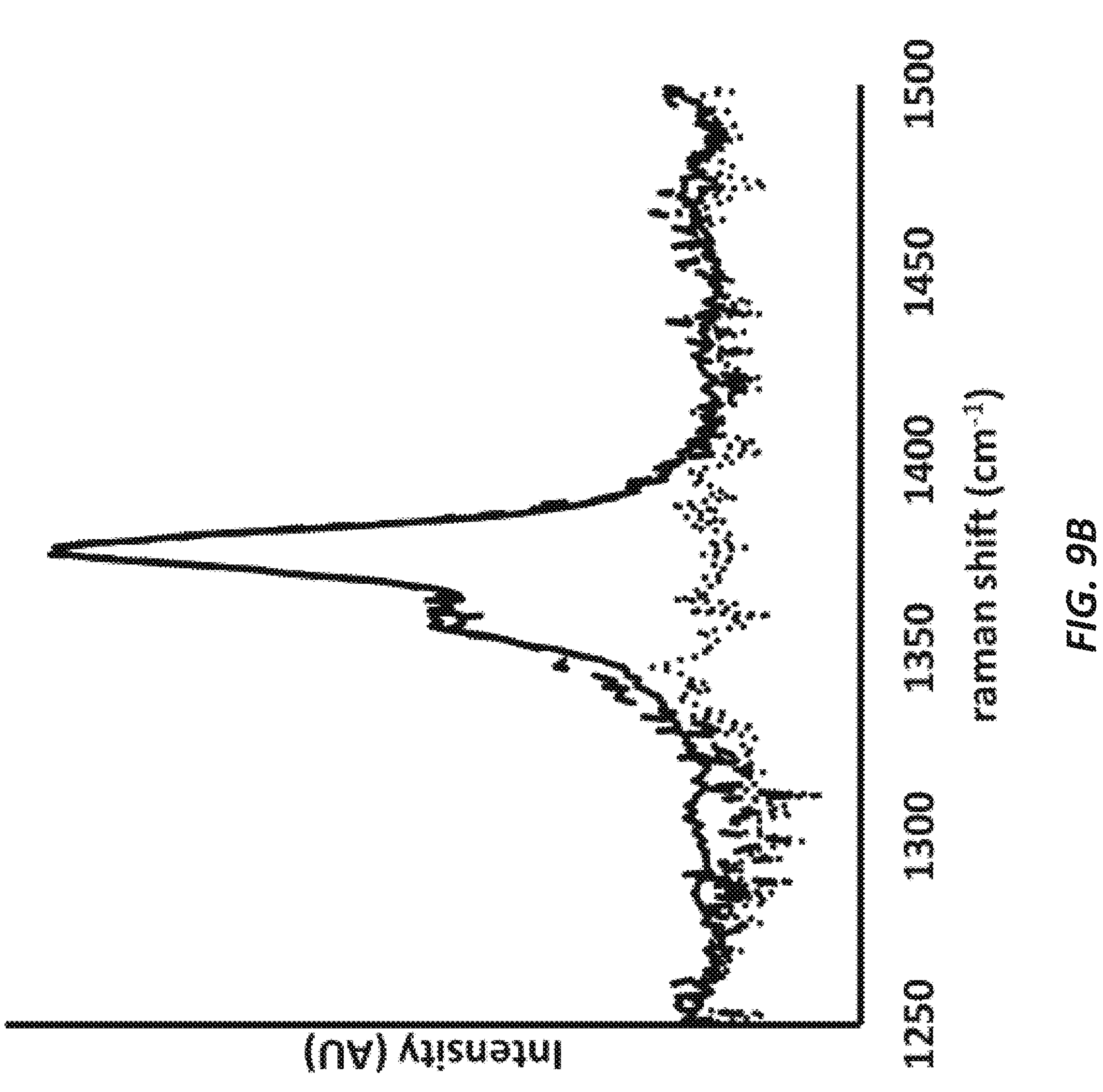
FIG. 9B is a graph of the resonance Raman spectrum from FIG. 9A analyzed with hemoglobin and cytochromes in the regression library.

FIGS. 9A and 9B show RRS measurements obtained from the surface of a blood perfused human liver during normothermic machine perfusion. FIG. 9A shows the results of analyzing the measured spectrum against a hemoglobin reference spectra library only. The regression analysis determines a weighting factor for each library spectrum, with the mathematical sum of the weighted spectra representing the best fit of the measured spectrum. The residual is the remainder of the measured result that is not explained by the regression. The regression analysis shown in FIG. 9A using a hemoglobin reference spectra library alone did not explain the full spectrum. The regression resulted in a significant residual, particularly in the v4 band between 1350 $cm^{-1}$ and 1380 $cm^{-1}$ that is characteristic of heme-containing chromophores, such as hemoglobin and mitochondrial cytochromes. Because the peaks from cytochromes are slightly shifted from the hemoglobin peaks, a dipole structure appears in this region due to the unexplained spectrum.

FIG. 9B shows the results of analyzing the same measured spectrum against a library containing hemoglobin and cytochrome reference spectra. When cytochromes are included in the regression library, the residual is reduced, suggesting that the unexplained residual resulted from cytochromes in the tissues. Because the fit of the measured spectrum is significantly better when the cytochrome reference library is included, the mitochondrial redox state can be isolated against a blood background in perfused human livers.

In this experimental analysis, the media and/or perfusate represents less than 5% of the total RRS signal, with most of the spectrum resulting from hemoglobin and mitochondria. The resolution of the spectrometer is adequate to distinguish small peak shifts, and the difference between the oxidized and reduced states are easily observable at 1371 cm-1 and 1357 cm-1 when excited by the 441 nm laser. The RRS system does not rely on individual peaks, however, instead applying the regression across the full range (700 cm-1 to 1500 cm-1) to determine the optimal addition of complete library spectra to explain the measured spectrum. The advantage of resonance Raman spectroscopy versus absorbance is that the spectra are highly specific to not only the oxidized and reduced states but to the spectra of similar chromophores such as cytochromes and hemoglobin. The specificity of the vibrational modes is not affected by the broad absorption bands, in fact, the strong Soret absorption band in the 400-450 nm region drives a several order of magnitude resonant enhancement of the Raman signal.

The RRS system can be utilized to develop a spectral library for the following chromophores derived from human tissues in both oxidized and reduced states: 1. Hemoglobin (Sigma Aldrich), 2. Beta Carotene (Sigma Aldrich), and 3. Whole Mitochondria (isolation). In order to tune the excitation wavelength and the analysis of the measured signal from human tissues, additional library reference spectra based on human sourced materials, especially mitochondria, are collected. For instance, whole mitochondria can be isolated and suspended in a 1 mL vial using a magnetic stirrer and 200 μl of sample. The mitochondria can be fully oxidized by exposure to oxygen or fully reduced by the addition of sodium dithionate. Integrated Raman spectra from the mitochondria can be collected, e.g., for a period of 10 minutes, and saved for use in the reference library.

Figure 10A:
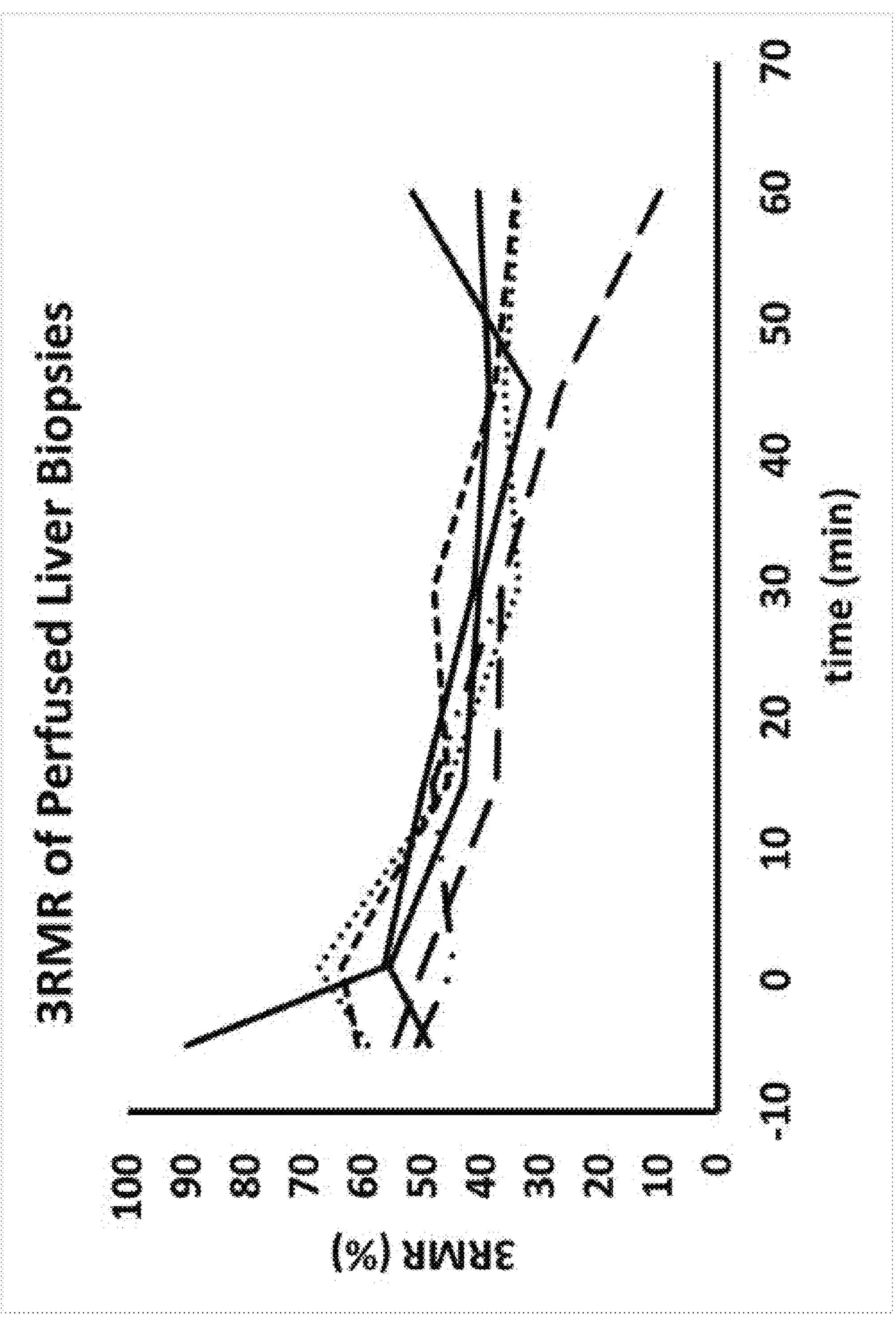
FIG. 10A is a graph of resonance Raman reduced mitochondrial ratios (3RMRs) from several rat liver biopsies during perfusion.
Figure 10B:
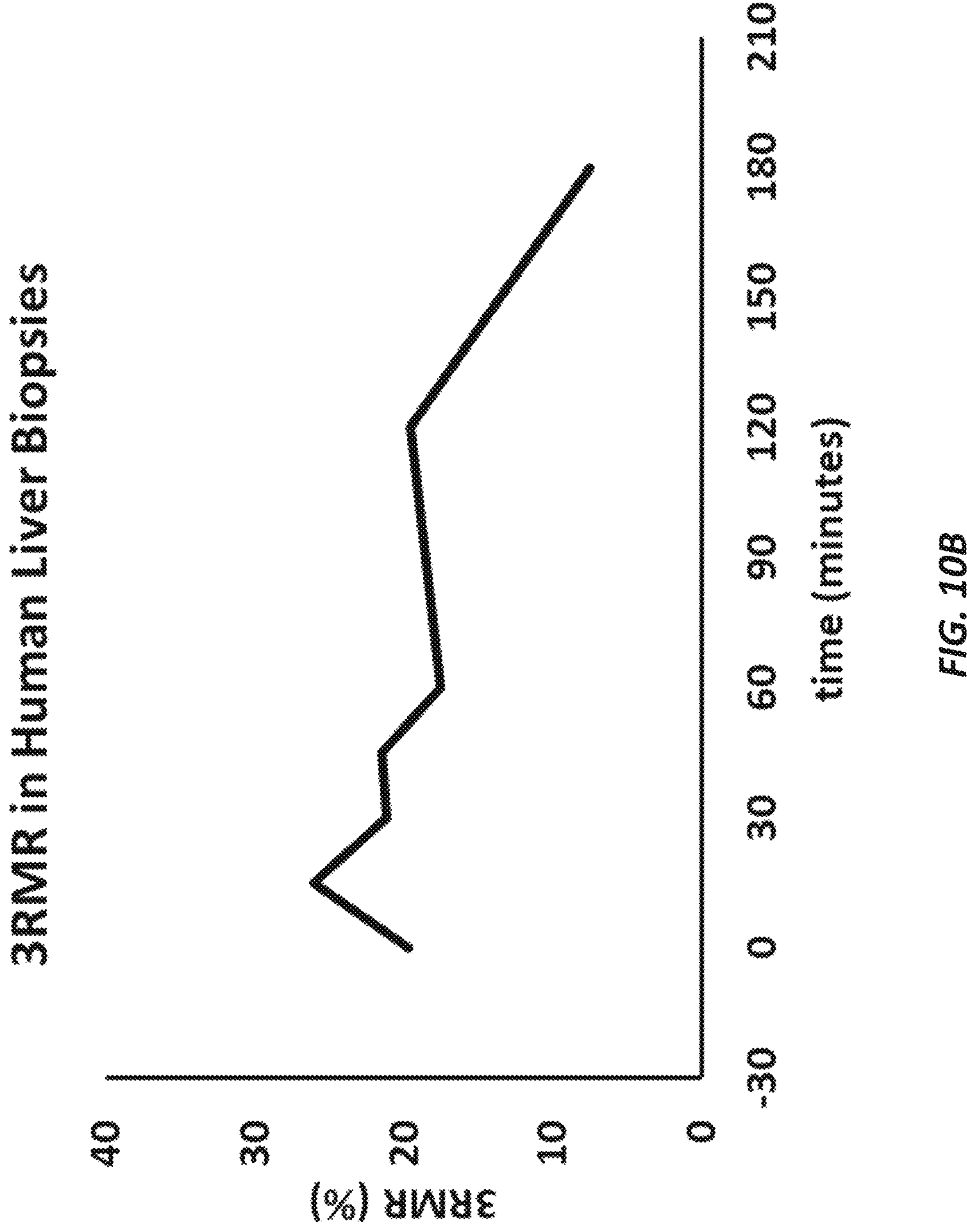
FIG. 10B is a graph of 3RMRs from a human liver biopsy during perfusion.

Prediction of Viability Using RRS Measurements During Perfusion of Small Tissue Samples Taken Via Biopsy from Donor Organs FIGS. 10A and 10B show a study to determine the feasibility of taking measurements from a liver tissue sample taken via biopsy. Samples were taken from rat (FIG. 10A) and human livers (FIG. 10B) and then perfused for a period of time, taking 3RMR measurements at 15-minute intervals. The signal strength was strong, and the 3RMR decreased during the ongoing perfusion though at a slower rate than was observed in the intact liver.

The RRS system can be used to quantify the state of cytochrome c in human liver. Reference spectra of cytochrome c in its membrane associated and free states can be used to assess its use as a marker of ischemic damage. Cytochrome c has been proposed to play a role in apoptosis through outer membrane permeabilization of the mitochondria. Reference spectra for both states can be used to investigate as a marker of ischemic tissue damage. Cytochrome c can be isolated using the method of Margoliash. Commercially available bovine cytochrome c (Sigma Aldrich) can also be compared. Oxidized and reduced reference spectra of both free and cardiolipin associated cytochrome c can be developed for use in the reference library.

Figure 11:
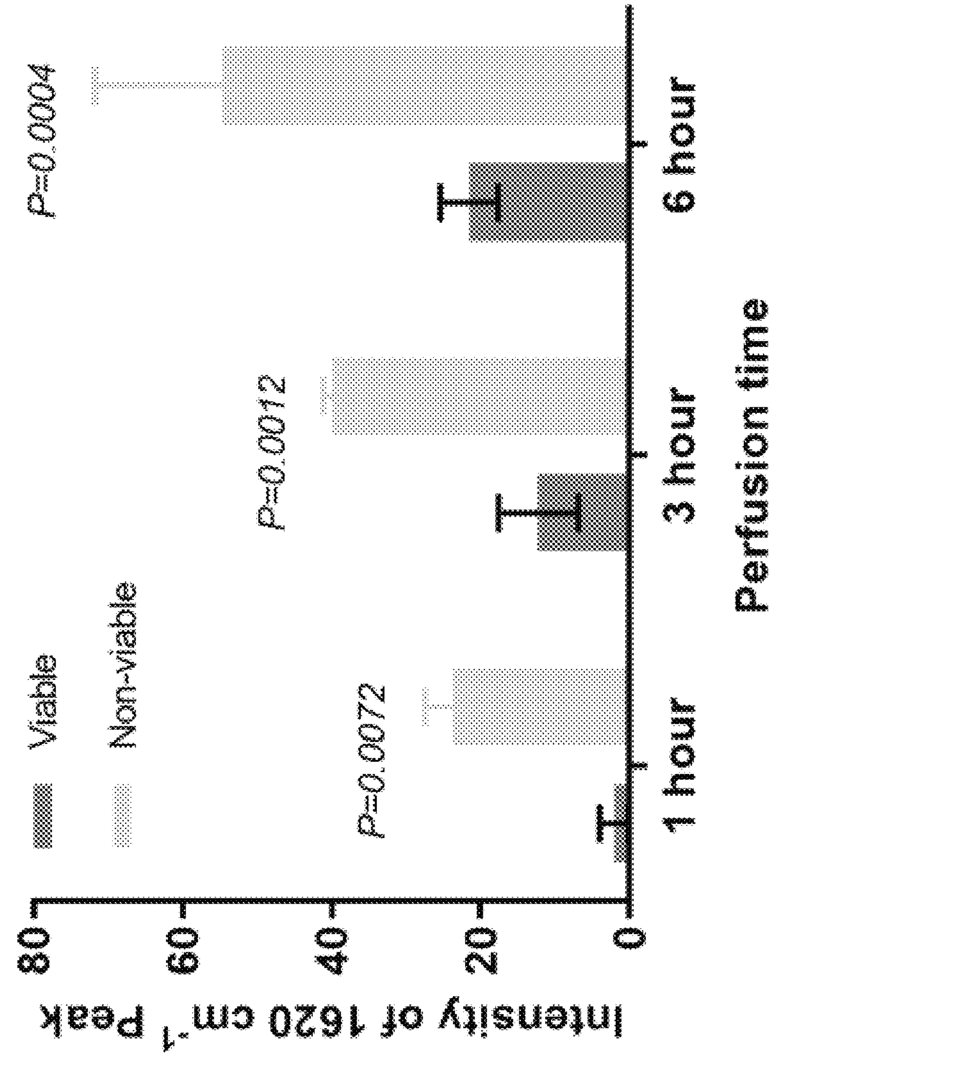
FIG. 11 is a graph of the intensity of a resonance Raman peak measured from perfusate during perfusion of viable and non-viable human livers subjected to 6 hours of normothermic machine perfusion in the presence of blood.

Prediction of Viability Using RRS Measurements of Perfusate During Tissue Sample Perfusion FIG. 11 shows a viability assessment of the perfusate sampled from human livers with a RRS system. For perfusate measurements, samples were collected by the same ports which is used to measure gas, pH, transaminase, etc., assessment. Perfusate samples were drawn using a syringe from a port in the perfusion tubing. RRS was used to look for mitochondrial breakdown products directly in recirculating perfusate. The composition of the perfusate may better reflect the whole organ and may act as a complimentary measurement to surface readings and core biopsies. Without being bound by any particular theory, it has been hypothesized that cytochrome c in circulating plasma is a marker of mitochondrial injury following periods of ischemia. The association of cytochrome c with cardiolipin in the outer mitochondrial membrane may induce permeability leading to apoptosis. In this process, the cytochrome c protein is unfolded, leading to changes in the Raman spectrum.

To demonstrate the feasibility of sampling the perfusate and using Raman spectroscopy to assess viability of human livers, the blood-based perfusate of 6 discarded human donor livers that were subjected to normothermic machine perfusion (NMP) was analyzed. The raw perfusate Raman spectrum was measured at 1, 3, and 6 hours of perfusion using a 441 nm excitation wavelength. A clear spectrum was obtained from the perfusate with distinct peaks at ~1267, ~1505, and ~1620 $cm^{-1}$, which are consistent with cardiolipin associated cytochrome c. The intensity of this spectrum significantly increased during perfusion for all livers. Four out of six livers met the transplantable viability criteria that are used in European clinical trials (i.e., viability parameters such as lactate, resistance, transaminases, bile production, and bile pH). These livers had significantly lower peak heights at all time points compared to the 2 livers that performed poorly during NMP (P=0.0072, P=0.0012, and P=0.0004 at T=1, T=3, and T=6 hours, respectively).

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of", "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of monitoring a biological tissue, the method comprising:

perfusing the biological tissue with a perfusate;

measuring a Raman spectrum of the perfusate after it circulates through the biological tissue;

quantifying a concentration of cytochrome c in the perfusate from the Raman spectrum; and determining a viability of the biological tissue based on the concentration of cytochrome c in the perfusate.

2. The method of claim 1, wherein the biological tissue is a biopsy sample obtained from a donor organ intended for transplant.

3. The method of claim 1, wherein:

measuring a Raman spectrum of the perfusate comprises measuring a series of Raman spectra of the perfusate over a period of time;

quantifying the concentration of cytochrome c in the perfusate comprises quantifying a change over time in the concentration of cytochrome c in the perfusate from the series of Raman spectra; and determining the viability of the biological tissue comprises determining the viability of the biological tissue based on the change over time of the concentration of cytochrome c in the perfusate.

4. The method of claim 1, wherein the biological tissue is a donor organ intended for transplant.

5. The method of claim 4, wherein the donor organ is a liver, a heart, a kidney, or a lung.

6. The method of claim 1, wherein measuring the Raman spectrum of the perfusate comprises contacting the perfusate with a probe.

7. The method of claim 1, further comprising warming the perfusate to 37° C. before perfusing the biological tissue with the perfusate.

8. The method of claim 1, wherein the perfusate comprises at least one of UW solution, William's E medium, or blood.

9. The method of claim 1, wherein quantifying the concentration of cytochrome c in the perfusate comprises analyzing the Raman spectrum using a reference library.

10. The method of claim 1, wherein measuring the Raman spectrum of the perfusate comprises exciting the perfusate with a Raman pump beam at a wavelength of about 400 nm to about 450 nm.

11. The method of claim 2, wherein the donor organ is a liver, a heart, a kidney, or a lung.

12. The method of claim 2, further comprising predicting a probability of rejection of the donor organ by a patient based on the viability of the biological tissue.

13. The method of claim 3, wherein measuring the series of Raman spectra of the perfusate comprises making standoff Raman spectra measurements of the perfusate.

14. The method of claim 3, further comprising quantifying a series of reduced mitochondrial ratios in the perfusate from the series of Raman spectra series of the perfusate.

15. The method of claim 14, further comprising identifying a trend in the series of reduced mitochondrial ratios in the perfusate over the period of time.

16. The method of claim 3, wherein the period of time is 30 minutes to 60 minutes.

17. The method of claim 3, wherein the series of Raman spectra of the perfusate comprises at least three Raman spectra.

* * * * *